(12) United States Patent
Sakuragi et al.

(10) Patent No.: US 10,564,233 B2
(45) Date of Patent: *Feb. 18, 2020

(54) MAGNETIC RESONANCE IMAGING APPARATUS AND CONTROL METHOD THEREFOR

(71) Applicant: HITACHI, LTD.

(72) Inventors: Kenta Sakuragi, Tokyo (JP); Hisako Nagao, Tokyo (JP); Masaharu Ono, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1099 days.

This patent is subject to a terminal disclaimer.

(21) Appl. No.: 14/897,066

(22) PCT Filed: Jun. 18, 2014

(86) PCT No.: PCT/JP2014/066096
§ 371 (c)(1),
(2) Date: Dec. 9, 2015

(87) PCT Pub. No.: WO2014/208409
PCT Pub. Date: Dec. 31, 2014

(65) Prior Publication Data
US 2016/0128606 A1     May 12, 2016

(30) Foreign Application Priority Data

Jun. 26, 2013  (JP) .................................. 2013-133690

(51) Int. Cl.
*G01R 33/00*       (2006.01)
*G01R 33/28*       (2006.01)
(Continued)

(52) U.S. Cl.
CPC ............ *G01R 33/288* (2013.01); *A61B 5/055* (2013.01); *A61B 5/0555* (2013.01); *A61B 5/742* (2013.01); *G01R 33/546* (2013.01); *G01R 33/58* (2013.01)

(58) Field of Classification Search
CPC .................................................... G01R 33/288
See application file for complete search history.

(56) References Cited

U.S. PATENT DOCUMENTS

2011/0109312 A1* 5/2011 Yamanaka ........... G01R 33/288
                                                                              324/309

FOREIGN PATENT DOCUMENTS

JP          5-269117 A      10/1993
JP       2006-95278 A       4/2006
(Continued)

OTHER PUBLICATIONS

International Search Report from International Application No. PCT/JP14/66096 dated Sep. 22, 2014.
(Continued)

*Primary Examiner* — Joseph M Santos Rodriguez
(74) *Attorney, Agent, or Firm* — Brundidge & Stanger, P.C.

(57) ABSTRACT

The magnetic resonance imaging apparatus includes: a calculation means for calculating the amount of absorption of electromagnetic waves into the object according to the emission of RF pulses in a part of the object or a bed position where imaging is scheduled; a means for setting imaging conditions, in which the calculated amount of absorption satisfies conditions of the specified value of the amount of absorption of electromagnetic waves, from the relationship between the calculated amount of absorption and the specified value of the amount of absorption of electromagnetic
(Continued)

waves; and a bed control device that controls a top plate according to the set imaging conditions.

3 Claims, 21 Drawing Sheets

(51) Int. Cl.
*A61B 5/055* (2006.01)
*A61B 5/00* (2006.01)
*G01R 33/54* (2006.01)
*G01R 33/58* (2006.01)

(56) References Cited

FOREIGN PATENT DOCUMENTS

| | | | |
|---|---|---|---|
| JP | 2007-526783 | A | 9/2007 |
| JP | 2007-275126 | A | 10/2007 |
| JP | 2008-302096 | A | 12/2008 |
| JP | 2009-82331 | A | 4/2009 |
| JP | 2010/001747 | A1 | 1/2010 |
| JP | 2011-517983 | A | 6/2011 |
| JP | 2011-130896 | A | 7/2011 |
| JP | 2011-143235 | A | 7/2011 |
| JP | 2014014391 | A | 1/2014 |

OTHER PUBLICATIONS

Japanese Office Action issued in Application No. 2014016358, dated Dec. 26, 2017.

\* cited by examiner

FIG. 7

| IMAGING PART | BED POSITION | W-basic | HEAD ABSORPTION RATE Rh |
|---|---|---|---|
| HEAD | L1 | Wbb1 | Rh1 |
| | L2 | Wbb2 | Rh2 |
| | L3 | Wbb3 | Rh3 |
| SHOULDER | L4 | Wbb4 | Rh4 |
| CHEST | L5 | Wbb5 | Rh5 |
| | L6 | Wbb6 | Rh6 |
| ABDOMEN | L7 | Wbb7 | Rh7 |
| | L8 | Wbb8 | Rh8 |
| PELVIS | L9 | Wbb9 | Rh9 |
| | L10 | Wbb10 | Rh10 |
| THIGH | L11 | Wbb11 | Rh11 |
| | L12 | Wbb12 | Rh12 |
| FOOT | L13 | Wbb13 | Rh13 |

FIG. 8

| IMAGING PART | BED POSITION | W-patient | HEAD ABSORPTION RATE Rh |
|---|---|---|---|
| HEAD | L1 | Wp1 | Rh1 |
| | L2 | Wp2 | Rh2 |
| | L3 | Wp3 | Rh3 |
| SHOULDER | L4 | Wp4 | Rh4 |
| CHEST | L5 | Wp5 | Rh5 |
| | L6 | Wp6 | Rh6 |
| ABDOMEN | L7 | Wp7 | Rh7 |
| | L8 | Wp8 | Rh8 |
| PELVIS | L9 | Wp9 | Rh9 |
| | L10 | Wp10 | Rh10 |
| THIGH | L11 | Wp11 | Rh11 |
| | L12 | Wp12 | Rh12 |
| FOOT | L13 | Wp13 | Rh13 |

| IMAGING ORDER 652 | SCAN NAME 654 | PART 656 | BED POSITION L 658 | SAR [SPECIFIED SAR VALUE] 660 | SCAN TIME 662 | WAITING TIME TW SECONDS 664 | MOVING SPEED SB OF BED (TOP PLATE) 666 |
|---|---|---|---|---|---|---|---|
| 1 | SCAN A | HEAD | 0 | S1<[S100] | ST1 | 0 | 0 |
| 2 | SCAN C | ABDOMEN | 500 | S3<[S200] | ST2 | 50 | SP2 |
| 3 | SCAN B | CHEST | 350 | S2<[S300] | ST3 | 20 | SP3 |
| ... | ... | ... | | | ... | ... | ... |
| | | | | | TOTAL | TOTAL | TOTAL OF MOVEMENT TIME |

870

OK 872

MAGNETIC RESONANCE IMAGING APPARATUS AND CONTROL METHOD THEREFOR

TECHINCAL FIELD

The present invention relates to a magnetic resonance imaging apparatus and a control method for a magnetic resonance imaging apparatus.

BACKGROUND ART

There is magnetic resonance imaging (hereinafter, referred to as "MRI") as a technique of imaging and displaying the internal tissue of an object, such as a human body, and an MRI apparatus using this technique is known. In this MRI apparatus, a static magnetic field is applied to the object from the outside, and a high frequency magnetic field pulse (hereinafter, referred to as an "RF pulse") that is a high frequency electromagnetic wave is further applied. Then, the nuclear spins of atoms that form the tissue of the object cause the precession, a nuclear magnetic resonance signal (hereinafter, referred to as an "NMR signal") generated when the nuclear spins return to a stable state is measured, and the shape or function of a measurement target part of the object, for example, shapes or functions of the head, chest, abdomen, limbs, and the like are imaged and displayed in a two-dimensional manner or in a three-dimensional manner using the NMR signal.

Images captured by the MRI apparatus are very effective for medical diagnosis. Accordingly, these images are widely used when diagnosing the state of illness or injury. An imaging target when the MRI apparatus captures a medical image is a human body as described above, and it is necessary to assume a state in which there is already a serious problem in health, such as injury or illness.

For this reason, it is necessary to pay close attention to safety. There is an international standard on safety "IEC 60601-2-33, 3rd edition" regarding electromagnetic waves used for imaging by the MRI apparatus. According to this international standard, the amount of absorption of RF pulses into the human body per unit time and unit mass is defined as a specific absorption rate (SAR), the upper limit of the SAR value is set, and imaging should be performed under the imaging conditions in which the upper limit is not exceeded. Restrictions on the amount of irradiation of electromagnetic waves have been demanded so that the electromagnetic waves exceeding the upper limit of the SAR value are not emitted to the human body, which is an imaging target, in imaging using the MRI apparatus. For safety, it is necessary to keep the restrictions based on the standard.

An example of a method of keeping the international regulations regarding the amount of irradiation of electromagnetic waves is disclosed in PTL 1. The method disclosed in PTL 1 is a method of using the MR signal for determining the position of the object on the bed. In order to determine the position of the object on the bed, an RF pulse is emitted to the object, an MR signal is detected from the entire body of the object, and the position of the object on the bed is determined based on the detection result and the output of RF pulses is determined so as not to exceed the upper limit of the SAR value based on the detection result.

CITATION LIST

Patent Literature

[PTL 1] U.S. Pat. No. 7,834,624

SUMMARY OF INVENTION

Technical Problem

In the method disclosed in PTL 1, an MI signal is detected over a wide range of an object placed on the bed, particularly, over the entire body of the object as shown in FIG. 3, while moving the object within the gantry of the MRI apparatus, and the position of the object on the bed is determined based on the detected MI signal and the output power of the RF pulses is determined so as not to exceed the upper limit of the SAR value.

In this method, it is difficult to improve the accuracy of the estimated value of the SAR value during the imaging of the object. Therefore, it is necessary to increase a safety margin in the determination of the output power of RF pulses. On the contrary, as a result of increasing the safety margin, the output of RF pulses is suppressed lower than necessary. If the output of RF pulses is made lower than necessary, for example, there is a risk that the captured image quality will be lowered. In addition, if the safety margin is small, the SAR value may exceed the estimated value of the SAR value, which has been estimated in advance, during the imaging, and the upper limit of the SAR value may be exceeded. In this case, the imaging should be stopped.

If the imaging is stopped on the way, the working efficiency is significantly reduced since the imaging operation should be repeated. Therefore, an MRI apparatus capable of estimating the SAR value with higher accuracy in advance and a control method therefor have been demanded.

It is an object of the invention to provide an MRI apparatus capable of estimating the SAR value with high accuracy and a control method therefor.

Solution to Problem

A magnetic resonance imaging apparatus of the invention includes: a bed including a top plate that moves an object placed thereon; a magnetic field generation means for generating a magnetic field in a space in which the object is located; an irradiation coil for irradiating the object with RF pulses; a means for detecting an NMR signal generated by the object and imaging the detected NMR signal; an input and output device for inputting or displaying imaging conditions; and a control device that calculates an amount of absorption of electromagnetic waves according to emission of the RF pulses to the object based on the input imaging conditions, determines whether or not the calculated amount of absorption satisfies conditions of a specified value of the amount of absorption of electromagnetic waves, and performs at least one of movement control of the top plate and irradiation control of the RF pulses in accordance with imaging conditions determined to satisfy the conditions of the specified value of the amount of absorption of electromagnetic waves, in imaging of the part or in imaging at the bed position.

Advantageous Effects of Invention

According to the invention, it is possible to obtain an MRI apparatus capable of estimating the SAR value in imaging with high accuracy and a control method therefor.

BRIEF DESCRIPTION OF DRAWINGS

FIG. 7 is an explanatory diagram for explaining a database of W-basic used for the calculation of the predicted SAR value.

FIG. 8 is an explanatory diagram for explaining the database of W-patient used for the calculation of the measured SAR value.

FIG. 14 is an explanatory diagram for explaining the display content of an imaging schedule display portion of a display.

DESCRIPTION OF EMBODIMENTS

Figure 1:
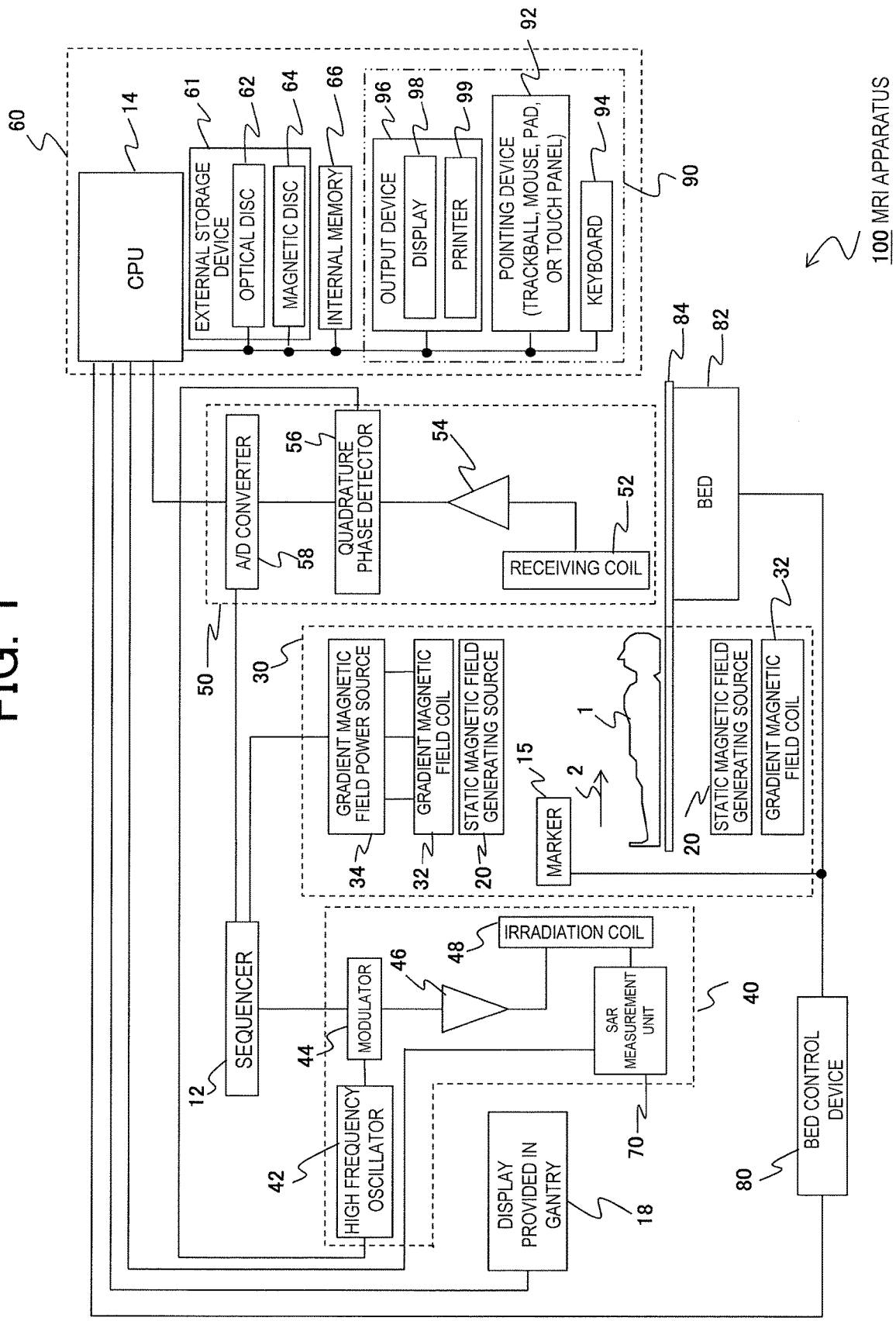
FIG. 1 is a block diagram showing the overall configuration of an MRI apparatus that is an embodiment of the invention.

Hereinafter, an embodiment of an MRI apparatus and a control method therefor to which the invention is applied will be described with reference to the diagrams. In the diagrams described below, components or steps having the same reference numerals have approximately the same configuration or approximately the same operation, and show approximately the same effect. Repeated explanation of these components or steps will be omitted.

[Basic configuration of an MRI apparatus 100]

FIG. 1 is a block diagram schematically showing the overall configuration of the MRI apparatus 100 that is an embodiment of the invention. MRI apparatus 100 is an apparatus that captures a tomographic image of an object 1 placed on a bed 82 using a nuclear magnetic resonance (hereinafter, referred to as NMR) phenomenon. The MRI apparatus 100 includes: a magnetic field generating system 30 including a static magnetic field generating source 20 and a gradient magnetic field generating coil 32; a transmission system 40; a receiving system 50; a signal processing system 60 including a central processing unit (hereinafter, referred to as a CPU) 14 and an input and output device 90; a bed control device 80 that controls the bed 82; a sequencer 12; and a marker 15. The static magnetic field generating source 20 and the gradient magnetic field coil 32 generate a static magnetic field and a gradient magnetic field in the imaging space formed in the central portion of the gantry.

The object 1 is guided to the imaging space in the gantry in a state of being placed on the bed 82, and, for example, magnetic fields generated by the static magnetic field generating source 20 and the gradient magnetic field coil 32 are applied to the object 1, and a high frequency magnetic field pulse (hereinafter, referred to as an RF pulse) is emitted from an irradiation coil 48 to the object 1. As a result, nuclei of atoms that form the body tissue of a part of the object 1 are excited, thereby inducing the NMR phenomenon. Nuclei generate an NMR signal due to the NMR phenomenon, and the NMR signal is received by a receiving coil 52 provided near the object 1. An image is formed by the received NMR signal, and is displayed on a display provided in an output device 96 of the signal processing system 60. The output device 96 includes not only the display but also a printer or various other output devices if necessary.

The magnetic field generating system 30 includes a gradient magnetic field coil 32 for each axis, which is provided to apply a gradient magnetic field in each of three axial directions of X, Y, and Z axes that are the coordinate system, that is, the stationary coordinate system of the MRI apparatus, and a gradient magnetic field power source 34 for driving the gradient magnetic field coil 32 for each axis. By driving the gradient magnetic field power source 34 of each gradient magnetic field coil according to the command from the sequencer 12, a gradient magnetic field Gx, Gy, or Gz is applied to the object 1 in the X, Y, or Z axis. At the time of MRI imaging, for example, a slice-direction gradient magnetic field pulse (Gs) is applied in a direction perpendicular to the slice surface, that is, an imaging section in order to set a slice surface for the object 1, and a phase-encoding-direction gradient magnetic field pulse (Gp) and a frequency-encoding-direction gradient magnetic field pulse (Gf) are applied in two remaining directions, which are perpendicular to the slice surface and are also perpendicular to each other, in order to encode the position information in each of the directions in the NMR signal.

The static magnetic field generating source 20 based on the horizontal magnetic field method that generates a uniform static magnetic field in a body axis direction 2 of the object 1 is used, and a permanent magnet type static magnetic field generating source, a normal conduction type static magnetic field generating source, or a superconducting type static magnetic field generating source is disposed around the object 1. In addition, the static magnetic field generating source 20 based on the vertical magnetic field method that generates a uniform static magnetic field in a direction perpendicular to the body axis in the space around the object 1 may be used. The basic idea is the same, and an example of using the horizontal magnetic field method will be described below as a representative example. However, as described above, the application of the invention is not limited to the horizontal magnetic field method.

The transmission system 40 emits an RF pulse to the object 1 in order to cause nuclear magnetic resonance in the nuclear spins of atoms that form the body tissue of the object 1, and includes a high frequency oscillator 42, a modulator 44, a high frequency amplifier 46, and the irradiation coil 48 that is a high frequency coil. The irradiation coil 48 is disposed near the object 1. The RF pulse output from the high frequency oscillator 42 is amplitude-modulated by the modulator 44 at the timing according to the command from the sequencer 12, and the amplitude-modulated RF pulse is amplified by the high frequency amplifier 46 and is then supplied to the irradiation coil 48. As a result, the RF pulse is emitted to the object 1. The amount of absorption of the RF pulse emitted from the irradiation coil 48 into the object 1 is measured by an SAR measurement unit 70.

The receiving system 50 has a function of detecting an NMR signal emitted by the NMR phenomenon, and includes a receiving coil 52 that is a high frequency coil, a signal amplifier 54, a quadrature phase detector 56, and an analog-to-digital converter (hereinafter, referred to as an A/D converter) 58. An NMR signal from a part of the object 1 that is excited by the RF pulse emitted from the irradiation coil 48 is received by the receiving coil 52 disposed near the object 1 and is amplified by the signal amplifier 54, and is divided into two signals perpendicular to each other by the quadrature phase detector 56 at a timing according to the command from the sequencer 12. Each of the two signals is converted into digital data by the A/D converter 58, and is transmitted to the signal processing system 60.

The irradiation coil 48 and the gradient magnetic field coil 32 are provided in the static magnetic field space (not shown) of the static magnetic field generating source 20, in which the object 1 is inserted, so as to face the object 1 in the case of the vertical magnetic field method and so as to surround the object 1 in the case of the horizontal magnetic field method. In addition, the receiving coil 52 is provided so as to face or surround the object 1. The sequencer 12 is a control means for performing control to repeatedly apply RF pulse and a gradient magnetic field pulse according to a predetermined pulse sequence, and operates under the control of the CPU 14 of the signal processing system 60 and transmits various commands, which are required to collect data of a tomographic image of the object 1, to the gradient magnetic field power source 34 of the magnetic field generating system 30, the transmission system 40, or the receiving system 50.

The bed control device 80 moves the bed 82 or transmits the position information of the bed 82 to the CPU 14 based on a moving distance signal received from the CPU 14. The moving distance signal may be generated by the input from the input and output device 90, or may be generated by the operation of a console that is separately provided in the MRI apparatus 100.

The marker 15 is formed by a device, such as a laser generator, and is attached to the object 1 in order to designate the position of a part, which becomes an imaging target, or the like. The marker 15 generates a laser, and controls the movement of the bed 82 so that the position of the marker 15 comes to a predetermined position of the imaging space, for example, the center of the magnetic field, by detecting the laser. Accordingly, it is possible to move the part of the object 1 designated by the marker 15 to the center of the magnetic field, for example.

The signal processing system 60 operates as a control device that performs command or data input processing for various kinds of operations or control, processing or control of various kinds of digital data, output processing such as display of a processing result, required data storage processing, processing for reading stored data, and the like. For this reason, the signal processing system 60 includes the input and output device 90, an external storage device 61 such as an optical disc 62 or a magnetic disc 64 for storing required data, an internal storage device (hereinafter, referred to as an internal memory) 66, and the CPU 14 operating as a control device that performs overall control of the MRI apparatus 100.

For example, when a digitized NMR signal is input from the receiving system 50 to the CPU 14 of the signal processing system 60, the CPU 14 generates a tomographic image of the object 1 by performing processing, such as signal processing or image reconstruction. In addition, the CPU 14 displays the tomographic image on a display 98 of the output device 96, and stores the tomographic image or required data in the magnetic disc 64 or the optical disc 62 of an external storage device 61 when necessary or based on the operation.

The input and output device 90 of the signal processing system 60 includes an input device for inputting various kinds of control information including various setting values used in the processing of the MRI apparatus 100 or various commands for operating the MRI apparatus 100 and an output device. Although not shown, the input and output device 90 includes a communication device for transmission and reception of information including an image to and from other devices or other systems. As the input device, the input and output device 90 includes a keyboard 94 and a pointing device 92 including a trackball, a mouse, a pad, and a touch panel. As the output device 96, the input and output device 90 includes the display 98 or a printer 99, for example. The input means includes a touch panel provided near the output device 96, such as the display 98, as the pointing device 92, and is configured such that the operator can direct the control of various processes of the MRI apparatus 100 interactively while observing the display of the display 98.

As the input and output device described above as the configuration of the input and output device 90, a plurality of sets of input and output devices may be provided when necessary. Not only is the input and output device 90 provided in the console of the MRI, but also a part of the input and output device 90 is provided in the gantry in order to improve workability. For example, the display 18 operates as a part of the output device of the input and output device 90, and is provided in the gantry (not shown). When the operator works near the gantry, it is possible to display information required for the operation on the display 18 and to input an instruction, a setting value, and the like from the display 18 corresponding to the display content.

The display 18 provided in the gantry having a display function or an input function operates as a part of the input and output device 90, and is connected to the CPU 14 similarly to the input and output device 90 so that the display of required information and the acquisition of operated input information are performed through the CPU 14. This function is very convenient for the operator who works near the gantry. Since it is not necessary to go to the location of the console one by one in order to check or input the display content, workability is improved. In the display 18 provided in the gantry, a display means and an input means are integrally formed, so that an instruction for operation can be given while observing the display of the display 18 provided in the gantry. In addition, the display content of the display 18 provided in the gantry and the display content of the display 98 may overlap, and input from the pointing device 92 or the keyboard 94 is possible instead of the input from the display 18 provided in the gantry.

As nuclides to be imaged by the MRI apparatus 100 described above, a hydrogen nucleus (hereinafter, referred to as proton) that is a main component material of the object 1, which is a human, is widely used clinically. In the MRI apparatus 100 of the present embodiment, the shapes or functions of parts, such as the head, abdomen, and limbs of the human body, are imaged in a two-dimensional or three-dimensional manner by imaging the information regarding the spatial distribution of the proton density or the spatial distribution of the relaxation time of the excitation state.

[Preparation of Imaging, and Setting of Imaging Schedule or Imaging Conditions]

Next, the procedure of capturing an MRI image of the object 1 in the MRI apparatus 100 will be described. The MRI apparatus 100 to which the invention is applied calculates an SAR value from the input object information or from the setting content for imaging and SAR value calculation value provided in advance in the MRI apparatus before performing imaging by irradiating the object 1 with RF pulses, and sets imaging conditions so that the calculated SAR value does not exceed the specified value that is set based on "IEC 60601-2-33, 3rd edition". Then, imaging is performed by irradiating the object 1 with RF pulses. In this manner, it is possible to effectively prevent a significant reduction in workability due to stopping of the imaging operation, which occurs when exceeding the specified value of the SAR value during the execution of imaging.

Figure 2:
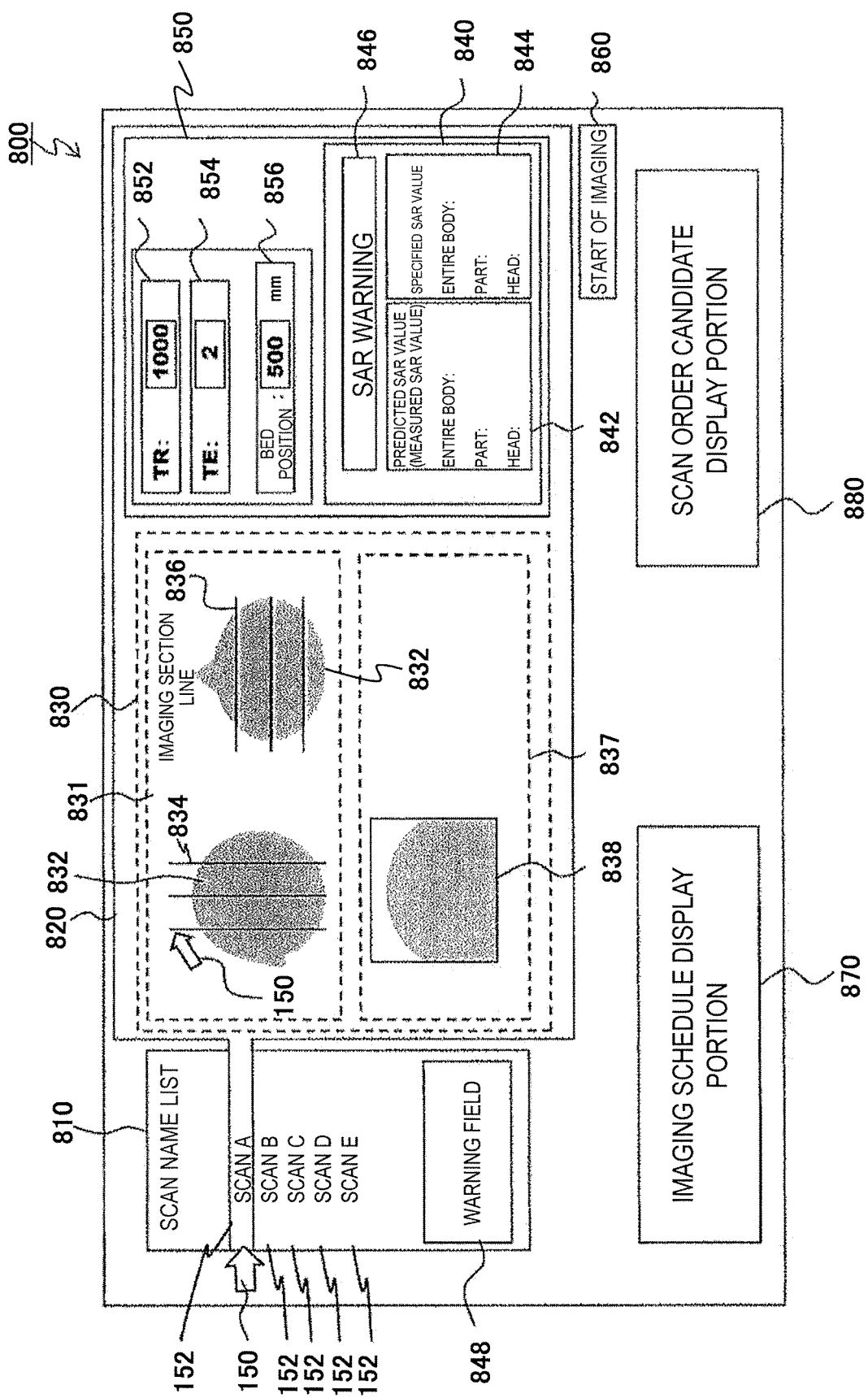
FIG. 2 is a display screen for inputting or setting the imaging schedule or imaging conditions.
Figure 3:
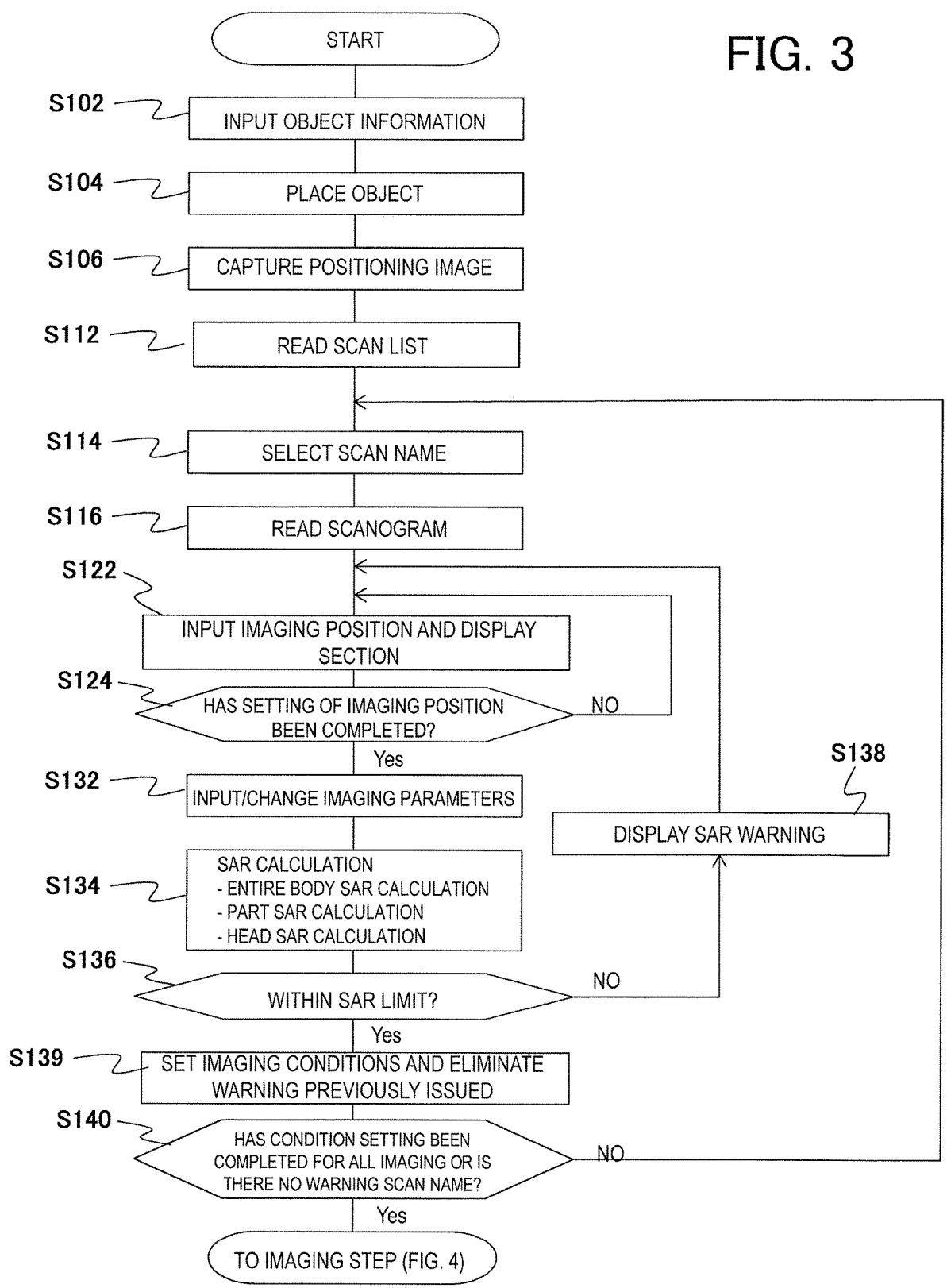
FIG. 3 is a flowchart for setting the imaging schedule or imaging conditions.

FIG. 2 is a setting image 800 that is used to set the imaging schedule and imaging conditions of the MRI apparatus 100, and is displayed on the display 98. The setting image 800 may be displayed not only on the display 98 but also on the display 18 provided in the gantry. FIG. 3 is a flowchart for setting the imaging conditions satisfying the conditions of the SAR.

The setting image 800 includes a scan list display portion 810 for displaying a list of scan names 152 illustrated in scans A to E, an imaging condition display portion 820 for displaying the imaging conditions of the selected scan name 152, an imaging schedule display portion 870 for displaying the imaging conditions of each scan name in the form of a list, and a scan order candidate display portion 880 for displaying the appropriate scan order determined by calculation. The imaging condition display portion 820 displays the imaging conditions, and can also be used when changing the displayed conditions or when inputting new conditions.

For example, a scan position 834 can be changed by selecting and moving the displayed scan position 834 with a cursor 150. In addition, the conditions of repetition time (TR) 852 can be changed by selecting the numerical value of the repetition time (TR) 852 with the cursor 150 and inputting a new numerical value. In addition, by performing an input operation by designating a target item or a position on the display image with the cursor 150, it is possible to input a new value. This is the same for other portions other than the illustrated item or position.

When a part to be imaged or a position, which is more specific than the part, is input in order through the input and output device 90, the scan name 152 for the imaging of each part or more specific indicated position that has been input is automatically assigned by the signal processing system 60, and is displayed in the scan list display portion 810 in the input order in the form of a list of scan names Each scan name 152 is assigned to the input part or the indicated position. The scan name 152 may be assigned to the part without assigning the scan name 152 to the indicated position.

In the present embodiment, however, the scan name 152 is assigned not only to a part but also to the more specific indicated position when necessary. Here, it is very convenient in the management of an imaging operation or in the operation for imaging to assume that the indicated position is a stop position where the bed 82 is stopped for imaging. For example, when imaging a plurality of imaging places in the head that are slightly away from each other, the bed 82 is moved corresponding to each imaging place even for the same head that is the same part, so that the position of the imaging place in the imaging space of the MRI is adjusted for each imaging place. By assigning the scan name 152 for each stop position of the bed 82, it is possible to set the imaging conditions including the position of the bed 82 for each stop position. In the results of the study of the inventors, the SAR value absorbed into the object 1 may change considerably for each imaging position. Therefore, in order to manage the SAR value with high accuracy, it is preferable to assign the scan name 152 for each stop position of the bed 82 with the stop position of the bed 82 as the indicated position.

The scan name 152 is assigned to the input part or the stop position of the bed 82, and the imaging conditions including the position of the bed are managed by the scan name 152. Therefore, it is possible to perform the writing or reading of the imaging conditions or imaging result of the scan name 152, which is selected with the scan name 152 as a keyword, and information regarding the object 1 into or from the external storage device 61 or the internal memory 66. Hereinafter, the imaging conditions including the position of the bed are referred to as a scan set. Each scan set is managed by the scan name 152. In a system including the MRI apparatus 100, if the object 1 is specified, it is possible to read an image, which is the result of imaging, or the related scan name 152 from the external storage device 61. Therefore, it is possible to read the imaging conditions or the SAR value at that time by specifying each scan name 152 from the list of the read scan A 152.

The scan name 152 is assigned in order of the input part or indicated position and is displayed on the scan list display portion 810, and imaging is performed in the order of display of the scan name 152. When the display order of the scan name 152 is changed by changing the display position by specifying the scan name 152 with the cursor 150, the imaging order is changed so as to follow the new display order. These operations can be performed not only by using the cursor 150 but also with a finger using a touch panel provided on the display surface of the display 98. This is the same for other items.

When one of the scan names shown as a list, for example, the scan A 152 is selected using the cursor 150 or the like, a scan set linked to the scan A 152 is read from the internal memory 66 or the external storage device 61, and the imaging conditions are displayed in the imaging condition display portion 820. For a case in which the imaging conditions of the scan A 152 have not yet been input or for an item for which the imaging conditions of the scan A 152 have not yet been input, only the item is displayed in a state in which there are no specific imaging conditions. It is possible to input the imaging conditions in blank fields of the imaging condition display portion 820 when necessary, or it is possible to change the imaging conditions with a new input operation even if the imaging conditions are already displayed.

The imaging conditions displayed in the imaging condition display portion 820 are linked to the selected scan name 152, and these are treated in the associated state in various operations or control therefor, such as imaging in the MRI apparatus 100, in the linked state. In this specification, a group of a series of related setting conditions or setting values including the imaging conditions linked to each scan name 152 may be referred to as a scan card, and each scan name 152 may be referred to as a scan card name. In the MRI apparatus 100, related information, such as imaging conditions, below the scan card name 152 is treated as a group. In this manner, by specifying each scan name 152, various setting values including the imaging conditions can be easily read and checked or changed. In addition, it is possible to perform writing into the internal memory 66 or the external storage device 61 or to perform an imaging operation. Therefore, it becomes easy to perform control, management, or an imaging operation.

The imaging condition display portion 820 includes: a positioning image display portion 830 for displaying a positioning image 832 for setting a scan position; an imaging parameter display portion 850 for inputting and displaying imaging parameters, such as the repetition time (TR) 852 for repeatedly applying the RF pulse, an echo time (TE) 854 that is a time until an NMR signal is actually received from the generation of the NMR signal, or a bed position 856 when performing imaging; an SAR value display portion 840 for displaying a calculated SAR value to be described later; and an imaging start mark 860 for operating the imaging start.

Position information indicating the bed position 856 is, for example, a relative position from the center of the magnetic field, and may be input by the operator. Instead of the input of the operator, the signal processing system 60 may calculate the movement position of the bed 82 from the positioning image, the position of an imaging section to be described later, and the like, so that the position information is automatically set. Similarly, also for the repetition time (TR) 852 or the echo time (TE) 854, the calculation result of the signal processing system 60 may be input and set. Alternatively, the operator may input the repetition time (TR) 852 or the echo time (TE) 854. The imaging start mark 860 to give a command for starting the operation of imaging is displayed in the imaging condition display portion 820, and a scan operation for imaging is started according to the conditions set by the imaging parameter display portion 850 by operating the imaging start mark 860.

A positioning image display portion 831 for displaying the positioning image 832 for setting the scan position 834 or a scan position 836, which is an imaging position, or an image display portion 837 in which a temporary sectional image 838 based on the set scan position 834 or 836 is displayed is provided in the positioning image display portion 830.

The positioning image 832 displayed in the positioning image display portion 831 is an image in which a wide range of the image of the object 1 is shown as, for example, a two-dimensional image such as an image in a side view or an image in a plan view (parietal side), or a three-dimensional image, or a one-dimensional image. The scan position 834 or the scan position 836 showing the position of the imaging section is displayed so as to overlap the positioning image 832. The scan position 834 or the scan position 836 has a function of setting which position of the sectional image (referred to as a slice image) of the object 1 is to be imaged. For example, the scan position 834 or the scan position 836 is set while moving the cursor 150 through the pointing device 92, such as a mouse or a touch panel, or the keyboard 94.

In addition, it is possible to change the scan position 834 or the scan position 836 that has already been set, or it is possible to newly add the position. For example, when the scan position 834 to be moved is selected by the cursor 150 and is moved to a movement target position, the scan position 836 is also moved automatically according to the movement of the selected scan position 834. By performing a setting operation when the scan position 834 has moved to an appropriate position, the new moved position becomes a new setting position. The scan position 836 is also displayed in the newly set position. The temporary sectional image 838 of the new scan position 834 or the scan position 836 is displayed. The positioning image 832 is an image for specifying the external shape of the object 1 or the positional relationship between the bed 82 and the object 1, and is not an image for imaging a detailed section. Therefore, the displayed sectional image 838 is not a detailed image but a very rough image for checking the sectional image. However, since it is possible to check whether or not the imaging position has been appropriately set, the positioning image 832 is very helpful.

In order to add the scan position 834 or the scan position 836, the scan position 834 or the scan position 836 can be newly added by designating a position to be added with the cursor 150 and performing a setting operation. In contrast, by selecting the scan position 834 or the scan position 836 that has already been set and performing an erasing operation, the scan position 834 or the scan position 836 that is set can be deleted.

In order to check the state of an image captured at the scan position 834 or the scan position 836 in advance, when a specific scan position is selected from a plurality of set scan positions 834 or scan positions 836 with the cursor 150, the temporary sectional image 838 at the selected scan position is displayed in the image display portion 837. In addition, when a plurality of scan positions are simultaneously designated by the cursor 150, a plurality of temporary sectional images 838 are displayed based on the plurality of designated scan positions.

In FIG. 2, an image for positioning (hereinafter, referred to as a scanogram) is displayed as the positioning image 832, and a sectional image of the scanogram is displayed in the temporary sectional image 838 based on the scan position selected by the cursor 150. When a specific scan name is selected by the cursor 150 as described above, imaging conditions linked to the selected scan name are displayed in the imaging condition display portion 820, and the set scan position is displayed in the positioning image display portion 830 of the imaging condition display portion 820. When a plurality of scan positions of the selected scan name are set, a plurality of scan positions 834 or a plurality of scan positions 836 for displaying the scan positions are displayed. By selecting a specific scan position from the plurality of scan positions 834 or the plurality of scan positions 836, it is possible to check the state of the captured image in advance. Thus, since it is possible to check the state of the captured image of the object 1 when imaging based on the scan list has actually been performed, it is possible to improve the reliability of imaging.

However, the method of using the scanogram of the object 1 for the setting of the imaging conditions is an example, and a standard model image that is read from the external storage device 61 may be used instead of the scanogram. Alternatively, a past image of the object 1 may be used. In the case of using a standard model image, if there is a difference between the actual size of the object 1 and the size of a model image to be used, the set positional relationship may be modified and specified by proportional calculation using the ratio of the size of the object 1 and the size of the model image.

In FIG. 2, the positioning image 832 or the temporary sectional image 838 corresponding to the scan A 152 selected by the cursor 150 is displayed in the image display portion 837. By performing display for making the selected scan name clear so that the relationship of the link between the selected scan name and the positioning image display portion 830 can be visually recognized, for example, by changing the color of the display to a color different from those for the other scan names, the visual effect is improved. The visual effect is also improved by the display format in which the selected scan A 152 and the imaging condition display portion 820 are connected as shown in FIG. 2 as an example (hereinafter, referred to as a tab display).

According to the study of the inventors, it has been found that the value of the SAR absorbed into the object 1 is greatly changed in many cases if the part of the object 1 is different. In addition, when the bed 82 is moved to perform imaging since the scan positions are separated from each other even though the imaging target part is the same, it has been found that the value of the SAR absorbed into the object 1 is changed if the bed 82 is moved. For this reason, it is desirable to determine the value of the SAR by predictive calculation for each part unit, or more specifically, for each stop position where the movement of the bed 82 is stopped for imaging and to set the imaging conditions based on the predicted value of the SAR. By managing the value of the SAR by performing predictive calculation of the value of the SAR for each stop position of the bed 82, the imaging conditions for imaging at each stop position of the bed 82 can be more appropriately set with higher accuracy while maintaining the regulations of the SAR. By setting the scan name 152 so as to correspond to the stop position of the bed 82, it is possible to finely set the imaging conditions for each stop position of the bed 82. For example, it is possible to set the irradiation output of the RF pulse with higher accuracy.

In the embodiment shown in FIG. 2, each scan name 152 displayed in the scan list display portion 810 is automatically set so as to match the input part or the bed stop position where imaging is performed. This is an example, and the determination conditions of the irradiation output of the RF pulse are different when the type of an image to be captured is different even if the bed stop position is the same. Therefore, it is better to assign a new scan name if the type of an image to be captured is different. When the setting conditions in the positioning image display portion 830 are different or when the setting conditions in the imaging parameter display portion 850 are different, it is desirable to set the imaging conditions by assigning different scan names.

[Imaging Condition Setting Operation]

The imaging condition setting operation of the MRI apparatus 100 will be described with reference to FIGS. 2 and 3. FIG. 2 is an image displayed on the display 98 in order to set the imaging conditions of the selected scan name 152 or to display the set imaging conditions, and FIG. 3 is a flowchart showing the content when the signal processing system 60 operates to set the imaging conditions. In step S102 in FIG. 3, information regarding the object 1 is input using the keyboard 94 or the pointing device 92. The operation of these inputs can be performed from the display 18 provided in the gantry, or can be performed using the input and output device provided in the bed. Although new information may be input, previously input data may be read and a part or all of the data may be used.

The input information is, for example, information specifying a part to be imaged, a stop position of the bed 82 for performing scheduled imaging, or the object 1, or information indicating the state of the body of the object 1.

Although the imaging conditions may be input in the possible range in step S102, the imaging conditions may be collectively input in the next steps since all imaging conditions cannot be input in this step. As information of a part to be imaged, for example, there is the head, chest, abdomen, or limbs. Such information is used for the imaging of the scanogram performed below or the setting of imaging conditions including imaging parameters.

In the specification of a part, there is a case in which the range of an imaging target is too large to be specified. In this case, it is possible to specify the range of the imaging target at the stop position of the bed 82. In the next steps, the stop position of the bed 82 may be set from the relationship with the captured scanogram, and the imaging scheduled position may be input by being specified at the stop position. The information specifying the object 1 is a name or the assigned number, for example. As information indicating the state of the body of the object 1, there is a weight, height, age, or sex. The weight or height of the object 1 can be used to replace the standard reference with a value corresponding to the object 1. For example, the imaging position, such as the stop position of the bed 82, is input as data relative to the standard and is converted into a value corresponding to the body of the object 1 using the height or the weight, and this can be used as imaging conditions.

The following embodiment will be described on the assumption that parts to be imaged are five parts of "head", "chest", "chest", "abdomen", and "foot". The information of a part input in step S102 is also used in the imaging of a scanogram to be performed below. Based on each part that has been input, the signal processing system 60 sets a scan name for imaging to be described below, creates the list of scan names in the order of input, and displays the list in the scan list display portion 810 of the setting image 800.

In step S104, the object 1 is placed on a top plate 84 of the bed 82, and the top plate 84 is moved to be disposed at a predetermined position in the gantry of the MRI apparatus 100. The positional relationship between the object 1 and the MRI apparatus 100 is determined so that the reference point of the object 1 matches the reference position of the imaging space. After the positional relationship between the object 1 and the MRI apparatus 100 is determined, by moving the top plate 84 of the bed 82 accurately using the bed control device 80, it is possible to control the bed 82 so that each part of the object 1 or the scan position 834 and the scan position 836 comes to a designated position in the measurement space of the MRI apparatus 100. In step S104, for example, the object 1 is placed and fixed to the top plate 84 of the bed 82, and the marker 15 that emits a laser is fixed to the reference position of the part of the object 1, for example, to the center. Position information of the reference position of the part of the object 1 designated by the laser from the marke 15 may be transmitted to the bed control device 80 and the top plate 84 of the bed 82 may be moved based on the position information, so that the reference point of the object 1 designated by the marker 15 comes to the center of the magnetic field that is the reference position of the magnetic field. In this manner, it is possible to determine the positional relationship between the position designated by the marke 15 of the object 1 and the MRI apparatus 100.

In step S106, a scanogram for performing a detailed setting of the scan position 834 or the scan position 836 for imaging is imaged. The scanogram that is an image for performing a detailed setting of the scan position does not need to have high resolution, and the resolution for setting the scan position is sufficient. Therefore, it is possible to set the strength of the emitted RF pulse to be weaker than the strength of the RF pulse at the time of original MRI imaging. For this reason, since the SAR at the time of imaging of the scanogram is less than the SAR at the time of original MRI imaging, the specified value of the SAR is hardly exceeded. However, in order to further improve safety, also in the imaging of the scanogram, it is checked whether or not the SAR exceeds the specified value by following the procedure described below, and then the imaging of the scanogram is performed. As a result, it is possible to further improve the safety. In addition, it is possible to prevent an abnormal situation, such as the stopping of imaging due to the SAR value exceeding the setting value during the imaging.

In the imaging of the scanogram in the above step S106, the signal processing system 60 determines a distance from the position of each part, that is, from the reference point by calculation based on the part information for examination that has been input in step S102, and performs imaging of the scanogram at the calculated position. In the example described above, the input examination parts are the head, chest, chest, abdomen, and foot, the signal processing system 60 determines the position of each part by calculation from the stored information of the standard position for the standard height of each part and the height of the object 1 input in step S102, and the top plate 84 of the bed 82 is moved through the bed control device 80 so as to move to the positions obtained by the calculation in order of the parts. The imaging of the scanogram of the corresponding part is performed at each of the bed positions.

The signal processing system 60 stores an image of the two-dimensional or three-dimensional scanogram of each captured part in the internal memory 66, the optical disc 62, or the magnetic disc 64.

In steps S112 to S124, the setting of the scan position in each scan name of the scan list is performed using the image of the scanogram captured in step S106. The signal processing system 60 assigns a scan name to each part or the bed position previously input in step S102, and stores the list of assigned scan names in an imaging condition storage section 606 of the internal memory 66. The list of scan names is read from the internal memory 66 stored in step S112, and is displayed in the scan list display portion 810 shown in FIG. 2. In step S114, when a scan name is selected from the list of scan names by the operator or by the operation of the signal processing system 60, if there are imaging conditions that are already set for the selected scan name, the imaging conditions are displayed in the imaging condition display portion 820. Before these conditions are input, the display area is secured, but the display column of the conditions is blank. An item to be input can be selected by designating the display column with the cursor 150.

When the conditions are input to the selected item, the input content is displayed, and is set by an operation, such as determination. When a scan name is automatically selected by the signal processing system 60, a scan is selected in a predetermined order. For example, the scan A at the head of the list is selected first.

In step S116, for a part that is the imaging target of the scan A that is the selected scan name, here, for the head, a scanogram that has been captured and stored in step 106 is read, and is displayed as the positioning image 832 in the positioning image display portion 830 shown in FIG. 2. In step S122, one scan position to be imaged by the scan A is first input to the displayed image 832. This embodiment is an example in which a scanogram is used as the image 832 and the input and setting of the scan position are performed by displaying the scanogram. However, the use of a scanogram is not essential, and a standard image or pattern showing a part may be used. For example, since the information of the height or the like of the object 1 is input in step S102, the image of a standard part may be used after being corrected by the features, such as the height of the object 1, when necessary. There is an effect that it is possible to set the scan position more accurately by simply using the scanogram.

In step S122, one of a plurality of scan positions in the target scan name is input using the pointing device 92 or the keyboard 94. For example, by moving the cursor 150 to the scan position using the pointing device 92 or the keyboard 94 and directing the determination, it is possible to set a scan position in a vertical or horizontal direction from the cursor 150. By inputting a scan position to each positioning image 832 that is displayed in a two-dimensional manner, the scan position that is an imaging surface is determined. Then, an image of the input imaging surface is displayed as the temporary sectional image 838. In this manner, one of the scan positions 834 and one of the corresponding scan positions 836 are input, and one of the scan positions is set by a determination operation. By repeating this operation, it is possible to set a plurality of scan positions that are managed in the scan name. Also for a scan position that has already been set, by selecting the already set scan position with the cursor 150, it is possible to move or delete the selected scan position. In addition, it is possible to perform resetting, such as adding or changing the scan position, using the pointing device 92 or the keyboard 94.

In step S124, it is determined whether or not all of the required scan positions have been set for the selected scan name. When all of the required scan positions have been set, the execution proceeds to the next step S132. On the other hand, when the setting of the scan position has not ended for the selected scan name, step S122 is executed again. Corresponding to the input scan position of the input scan position 834 or the scan position 836, the temporary sectional image 838 as an image is displayed in the image display portion 837 of the positioning image display portion 830. The case in which each scan name includes one scan position is rare, and each scan name includes a plurality of scan positions and these series of scan positions can be managed and treated as a set.

When it is determined that all of the scan positions managed by the selected scan name have been set in step S124, the input and setting of parameters for imaging are performed for the scan A that is the selected scan name in step S132. The imaging parameters input in step S132 are the repetition time (TR) 852 of high frequency pulses for imaging described above, the echo time (TE) 854, the bed position 856, and the like. There are various parameters for imaging, and required parameters are input and set in step S132.

When the imaging conditions including the scan position of the scan name selected in step S132 are roughly input and set, for the confirmation of safety, the signal processing system 60 performs predictive calculation of the SAR in order to check whether or not the condition that the SAR value is equal to or less than the specified value is satisfied in the case of imaging under the imaging conditions of the selected scan name in step S134. The result of the predictive calculation performed by the signal processing system 60 is displayed as an SAR value 842 in the SAR value display portion 840 of the imaging condition display portion 820 shown in FIG. 2. In contrast to this, a specified SAR value 844 that should not be exceeded is displayed in the SAR value display portion 840.

Here, equations for performing the predictive calculation of the SAR are expressed as (Equation 1), (Equation 2), and (Equation 3).

$$\text{Predicted entire body } SAR(W/kg) = \frac{W - \text{basic} \frac{\text{Power } seq(W)}{\text{object weight } M(kg)}}$$ [Equation 1]

$$\text{Predicted body part } SAR(W/kg) = W - \text{basic} \frac{\text{Power } seq(W)}{\text{part mass of body in irradiation range } m_p(kg)}$$ [Equation 2]

$$\text{Predicted head } SAR(W/kg) = W - \text{basic} \frac{\text{Power } seq(W)}{\text{head mass } m_h(kg)} \times R_h$$ [Equation 3]

In (Equation 1), (Equation 2), and (Equation 3), Power seq (W) indicates Power sequence, and is a value obtained when the signal processing system 60 calculates the energy of the RF pulse emitted by the irradiation coil 48 based on the imaging parameters. In addition, W-basic is an SAR absorption rate, for example, a statistical average value of the SAR absorption rates when irradiating each part of a human, who is an object, with RF pulses. The entire body SAR defined by (Equation 1) is a numerical value obtained by dividing the energy of electromagnetic waves absorbed into the entire body of the object by the energy of electromagnetic waves of RF pulses by the mass of the object. The body part SAR defined by (Equation 2) is obtained by dividing the energy of electromagnetic waves absorbed into a desired part of the object by the mass of the desired part of the object. The head SAR defined by (Equation 3) is a value obtained by multiplying the entire body SAR by a head absorption rate Rh and dividing the result by the head mass.

Here, as described above, the specified SAR value is an SAR upper limit that should not be exceeded, and this is a value defined by a predetermined average time. Therefore, by increasing the waiting time to be described later, the time average of the SAR absorption rate is reduced. As a result, since the SAR value calculated by each equation is lower than the specified SAR value described above, the prescribed conditions are satisfied.

The details of the predictive calculation of the SAR using (Equation 1), (Equation 2), and (Equation 3) will be described below. The predictive calculation result of the SAR based on (Equation 1), (Equation 2), and (Equation 3) is displayed as the SAR value 842 in the SAR value display portion 840. When the predictive calculation result of the SAR exceeds the specified SAR value 844, a warning 846 is displayed in the SAR value display portion 840, and a scan name at this time is displayed in a warning column 848. The warning of the warning column 848 continues to be displayed even after the selected scan name is switched to another scan name Therefore, when a plurality of scan names are warning targets, the plurality of scan names are displayed in the warning column 848 for warning. On the other hand, the display of the warning 846 is performed for the selected scan name, and no warning is displayed in the warning 846 when a newly selected scan name is not a warning target. The SAR value 842 is displayed corresponding to the selected scan name and the specified SAR value 844 is also displayed corresponding to the selected scan name, and the warning 846 is displayed under the conditions in which the SAR value 842 exceeds the specified SAR value 844.

The signal processing system 60 determines whether or not each predictive calculation result calculated in step S134 exceeds the specified SAR value 844 provided corresponding thereto by executing step S136. When at least one of the predictive calculation results exceeds the specified SAR value 844 provided corresponding thereto, the signal processing system 60 executes step S138 to display the warning 846 in the SAR value display portion 840 shown in FIG. 2 and display the target scan name in the warning column 848 of the scan list display portion 810. In this case, imaging parameters or imaging conditions including the scan position are reset so that a 6-minute average and a 10-second average of the predictive calculation results do not exceed the specified SAR value 844.

For the resetting of imaging parameters or imaging conditions including the scan position, the signal processing system 60 executes steps S122 and S132 again. Here, it is possible to reduce the SAR value by reducing the number of imaging shown at the scan position 834 or the scan position 836 or by changing imaging parameters in step S132, and new imaging conditions are input and set. Then, the predictive calculation of the SAR is performed again in step S134. Then, in step S136, it is determined whether or not the predictive calculation result under the newly input imaging conditions exceeds the corresponding specified SAR value. Thus, it is possible to determine the imaging conditions under the condition that the specified SAR value 844 is not exceeded.

When it is determined that the predictive calculation result does not exceed the specified SAR value in step S136, the execution of the signal processing system 60 proceeds to step S139 in which the input imaging conditions are set and the corresponding warning is eliminated when a warning has been issued in the past in step S138 and the warning is displayed in the warning column 848 or in the warning 846. When the operator selects another scan name 152 in a state in which a warning is displayed in the warning column 848, the procedure from step S116 is performed for the newly selected scan name 152. In this case, the imaging conditions regarding the scan name 152 for which the warning is displayed are improved, and the display of the warning is not eliminated as long as the predictive calculation result exceed the specified SAR value. Therefore, safety regarding the specified SAR value 844 is maintained.

The above explanation has been given with the selected scan A as a representative example. However, it is determined whether or not the imaging conditions have been set for all of the scan names displayed in the scan list display portion 810 in step S140, and the execution of the signal processing system 60 proceeds from step S140 to step S114 when there is a scan name for which no imaging conditions are set. Then, a scan name for which the imaging conditions are to be input is selected, the input of imaging conditions and the predictive calculation of the SAR under the input imaging conditions are performed again, and the imaging conditions are set under the condition that the predictive calculation result of the SAR does not exceed the specified SAR value 844. In this manner, imaging conditions are set for each scan name displayed in the scan list display portion 810. Then, the execution of the signal processing system 60 proceeds to the flowchart of the imaging operation described in FIG. 4. When there is the scan name 152 for which a warning is displayed in the warning column 848, the execution proceeds from step S140 to step S114 in which the scan name 152, for which a warning is displayed in the warning column 848, is selected, and imaging conditions in which the predictive calculation result does not exceed the specified SAR value are set. The scan position or imaging conditions managed by each scan name are used as a scan card, and each scan name is stored and managed as a unit of a file in the internal memory 66, the optical disc 62, and the magnetic disc 64.

When the operator wants to change the scan position or the imaging parameters, the operator selects a scan name displayed in the scan list display portion 810 by operating the cursor 150 regardless of the execution position of the above flowchart shown in FIG. 3. Then, the imaging conditions of the selected scan name are displayed in the imaging condition display portion 820. In addition, it is possible to change the already set imaging conditions by selecting the target imaging conditions with the cursor 150. After changing the imaging conditions, the SAR value is calculated under the changed imaging conditions in step S134, and it is determined whether or not the predictive calculation result of the SAR exceeds the specified value in step S136. When it is determined that the predictive calculation result does not exceed the specified SAR value in step S136, newly changed imaging conditions are set in step S139. In addition, when a warning has been issued previously in step S138 and the warning is displayed in the warning column 848, the warning is eliminated.

As described above, it is possible to perform the predictive calculation of the SAR and to set the imaging conditions so that the predictive calculation result does not exceed the specified value of the SAR. Therefore, safety is further improved. In addition, since it is possible to prevent the occurrence of an abnormal situation in which the SAR value exceeds the specified value of the SAR during actual imaging, it is possible to prevent a situation, such as the stopping of imaging due to the occurrence of the abnormal situation.

Figure 4:
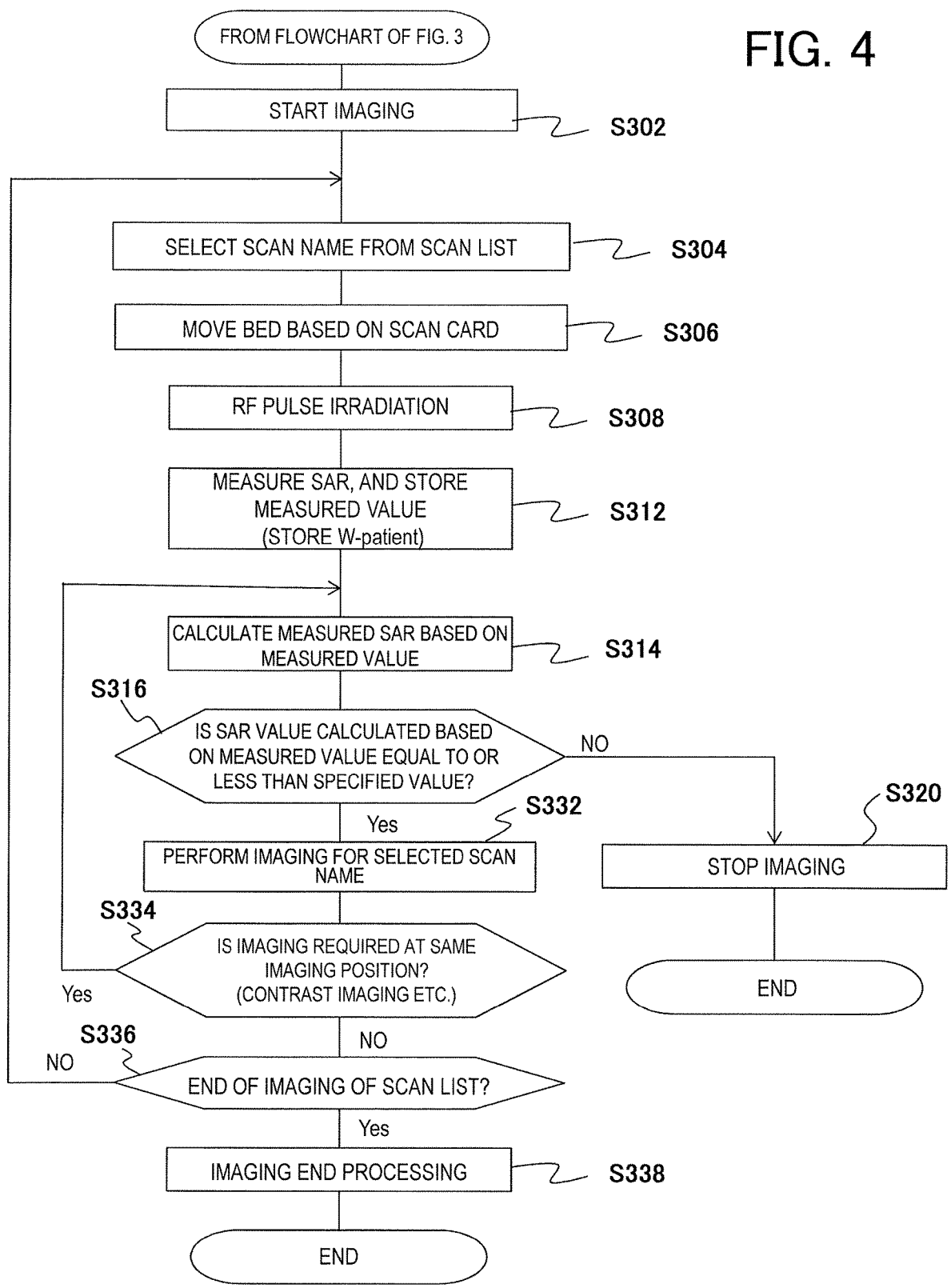
FIG. 4 is a flowchart showing the imaging operation of the MRI apparatus to which the invention is applied.

FIG. 4 is a flowchart showing the imaging operation of the MRI described. When the imaging start mark 860 displayed in the setting image 800 shown in FIG. 2 is operated or when the imaging start key of the input and output device 90 is selected, the signal processing system 60 executes step S302 in FIG. 4, and the MRI apparatus 100 starts the imaging operation. In step S304, the signal processing system 60 selects automatically a scan name at the head displayed in the scan list display portion 810. The order of the scan name displayed in the scan list display portion 810 indicates an imaging order, and the scan name located at the head is selected first by the signal processing system 60. The signal processing system 60 reads the scan card of the selected scan name, and controls the bed 82 based on the imaging conditions of the read scan card in step S306. The control of the bed 82 is performed by transmitting a control command to the bed control device 80 from the signal processing system 60. The top plate 84 of the bed 82 is controlled according to the imaging conditions so that the first imaging part of the object 1 is located, for example, at the center of the gradient magnetic field that is the reference position of the imaging space.

Then, in step S308, RF pulses based on the set imaging conditions are emitted from the irradiation coil 48. Based on the emitted RF pulses, the SAR measurement unit 70 calculates the SAR absorption rate of the individual object 1 by measurement in step S312. The SAR absorption rate (hereinafter, referred to as W-patient) of the individual object 1 that has been calculated based on the measurement is further stored in the internal memory 66 or the optical disc 62 in step S312, and is stored in the magnetic disc 64 when necessary. Here, the SAR measurement unit 70 is a device that calculates a more accurate W-patient corresponding to the object 1. There is no need to measure the W-patient itself as a measurement value, and any device that calculates the W-patient using the physical quantity measured based on the measured object 1 may be used.

In step S314, based on the W-patient, the signal processing system 60 calculates an SAR value (referred to as a measured SAR value) using the following (Equation 4), (Equation 5), and (Equation 6). The measured SAR value is calculated, and it is determined whether or not the calculated measured SAR value exceeds the specified SAR value in step S316. Based on the imaging schedule and the W-patient that have been input, predictive calculation of the measured SAR value to be executed later is performed in step S314, and it is determined whether or not the measured SAR value obtained by the predictive calculation exceeds the specified value of the SAR in step S316. The SAR measurement unit 70 measures the W-patient based on the RF pulses emitted for the imaging of the selected part, and the signal processing system 60 calculates the measured SAR value using the measured W-patient in step S314. However, when the W-patient of the target part is not present or when the W-patient of the target bed position L is not present, W-patient that is close in terms of a position, among the W-patient that is already present, is selected and the measured SAR value is calculated based on the imaging schedule, such as the imaging conditions, in step S314. Hereinafter, the calculation of the SAR value using the W-patient will be referred to as measured SAR value calculation. In addition, the calculation result will be referred to as a measured SAR value.

When the measured SAR value exceeds the specified value of the SAR, the execution of the signal processing system 60 proceeds to step S320 to stop the imaging operation. When it is determined that the measured SAR value (step S314) calculated using the W-patient in step S312 does not exceed the specified value of the SAR, step S332 is executed to execute the scheduled imaging operation. There is a case in which the same scan position is repeatedly imaged even though this is a special case. In this case, the execution returns again from step S334 to step S314 to repeat the imaging in the same procedure.

Then, the process returns from step S336 to step S304 in which the next scan name described in the scan list display portion 810 is selected, the imaging operation is similarly repeated, and the imaging of the selected scan name is performed. After completing the imaging for all of the scan names described in the scan list display portion 810 by repeating the imaging in the above-described procedure for all of the scan names described in the scan list display portion 810, the signal processing system 60 determines the end of the imaging in step S336, and the signal processing system 60 performs processing for ending the imaging of the MRI in step S338 to end the series of imaging operations.

In the flowchart shown in FIG. 4, the signal processing system 60 calculates a measured SAR value based on the W-patient based on the measurement in step S314, determines whether or not the calculation result of the measured SAR value exceeds the specified SAR value, and stops the imaging operation of the MRI when the calculation result of the measured SAR value exceeds the specified SAR value or when it is predicted that the specified value will be exceeded in a future imaging operation. Through this operation, it is possible to further improve safety. In addition, it is possible to reduce the waste of imaging operation.

Through the predictive calculation of the SAR described in the flowchart of FIG. 3, it is predicted whether or not there is a possibility that the SAR value will exceed the specified value during the actual imaging operation. When there is a possibility that the SAR value will exceed the specified value, it is possible to avoid wasteful imaging operation that the imaging operation should be stopped from the relationship of the SAR by changing the imaging conditions. In addition, by calculating the measured SAR value using the W-patient described in FIG. 4, it is possible to perform the predictive calculation of the SAR value with very high accuracy before the actual imaging operation. In addition, even if the imaging operation has started, it is possible to determine in the early stage and with very high accuracy whether or not the SAR value will exceed the specified SAR value in the imaging operation to be performed from now. This improves safety, and it is possible to prevent waste, such as the stopping of the imaging operation.

The measured SAR value is calculated from the W-patient according to the irradiation of RF pulses for imaging based on the imaging conditions, and measured SAR monitoring, which is for monitoring whether or not the measured SAR value that has been calculated with high accuracy exceeds the specified SAR value, is performed while performing the imaging operation as described in FIG. 4. By performing the monitoring so that the measured SAR value for the object 1 does not exceed the specified SAR value, the final safety is maintained. In the embodiment described in FIG. 4, the operation of imaging the object 1 and the operation of monitoring the measured SAR value are included in a series of flowcharts. The operation of imaging the object 1 and the operation of monitoring the measured SAR value may be independently performed by programs that are separately executed. By performing the imaging operation and the SAR monitoring operation in FIG. 4 in separate different programs, the SAR monitoring operation can be performed in a state in which the SAR monitoring operation is hardly restricted by the imaging operation. Therefore, it is possible to further improve the effect described above. The operation will be described with reference to the flowchart shown in FIG. 5. Steps having the same reference numerals as the reference numerals described in FIG. 4 show approximately the same operation, and show approximately the same effect. Explanation of the steps having reference numerals that have already been described will be omitted.

Figure 5:
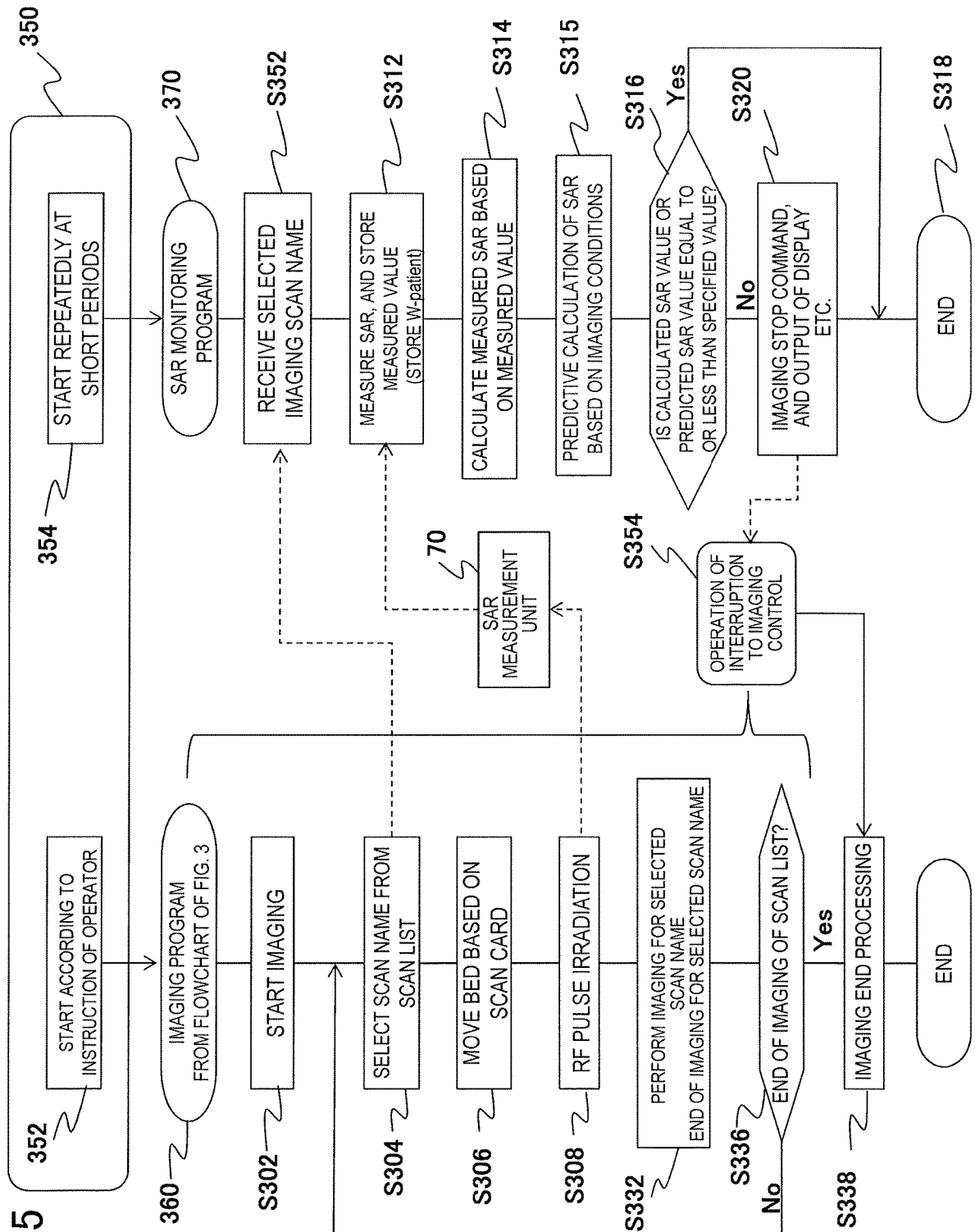
FIG. 5 is a flowchart showing another embodiment of the flowchart of the imaging operation shown in FIG. 4.

The flowchart shown in FIG. 5 shows the operation based on an imaging program 360 for performing an imaging operation based on the scan list described in the scan list display portion 810 in FIG. 2, a monitoring program 370 for performing the above-described SAR monitoring, and a management program 350 for managing the imaging program 360 or the monitoring program 370. These programs are stored in a storage section of the internal memory 66 of the signal processing system 60 or an external storage device, for example, a storage section of the magnetic disc 64 together with various programs for operating the signal processing system 60 described with reference to FIG. 2. By the execution of the imaging program 360 by the signal processing system 60, steps S302 to S308 and steps S332 to S338 are executed.

Since the basic operation of steps S302 to S308 and steps S332 to S338 has already been described, the detailed explanation thereof will be omitted. In step S304, scan names for imaging are sequentially selected from the list of scan names assigned corresponding to the imaging target part or the bed position where imaging is to be performed. In step S306, the imaging conditions of the selected scan name selected are searched for, and the bed 82 is controlled. In step S308, RF pulses are emitted to perform imaging. After all imaging operations at the scan positions in the selected scan name are completed, the execution of the signal processing system 60 proceeds from step S336 to step S304 to select a scan name for the next imaging in step S306. After the signal processing system 60 executes steps S308 and S332 to complete the imaging at all scan positions in the selected scan name, a scan name for the next imaging is selected in step S304. When the imaging operation for all scan names registered in the list of scan names has been completed as described above, the signal processing system 60 performs processing for ending the imaging in step S338, so that the imaging operation is ended.

The signal processing system 60 executes the monitoring program 370, which operates separately from the imaging program 360, and is for monitoring whether or not the measured SAR value exceeds the specified SAR value, thereby executing step S352 or steps S312 to S318 and executing step S320. The execution of the imaging program 360 or the monitoring program 370 is controlled by system software 350. The system software 350 is, for example, an operating system (OS), and manages various kinds of application software for controlling the hardware provided in the MRI apparatus 100 or for performing various kinds of operation or monitoring and controls the start, execution, or the like of each application software. The system software 350 is stored in a storage section of the internal memory 66 of the signal processing system 60 or a storage section of the external storage device 61.

When the operator operates the imaging start mark 860 displayed in the setting image 800 described in FIG. 2 or operates the imaging start key provided in the input and output device 90, the system software 350 starts the imaging program 360 as corresponding application software based on this operation, and the signal processing system 60 executes step S302. The system software 350 starts the imaging program 360 through the starting means 352 in response to the operation of the operator, and the starting means 354 starts the monitoring program 370 repeatedly at predetermined periods. In the monitoring program 370, when a scan name described in the scan list display portion 810 is specified in step S304 of the imaging program 360, the monitoring program 370 receives information on the specified scan name in step S352. Based on the received scan name information, the monitoring program 370 sets the scan name received in step S304 as a target scan name for which the measured SAR value is to be further calculated in step S352. The scan name receiving method can be realized, for example, by writing the information of the scan name selected in step S304 in the specific address of the internal memory 66 using the imaging program 360 and reading the selected scan name from the specific address in step S352 of the monitoring program 370.

The W-patient that the SAR measurement unit 70 outputs according to the irradiation of RF pulses from the irradiation coil 48 in step S308 of the imaging program 360 is repeatedly acquired in step S312 of the monitoring program 370, and the measured SAR value is calculated using the W-patient in step S314. In addition, according to the future imaging schedule and the imaging conditions, predictive calculation regarding the measured SAR is performed using the W-patient in step S314.

In step S316, it is determined whether or not the calculation result of the SAR in step S314 or the predicted calculation result of the SAR in step S314 exceeds the specified SAR value. When the calculation result of the SAR in step S314 or the predicted calculation result of the SAR in step S314 does not exceed the specified SAR value, the execution of the signal processing system 60 proceeds from step S316 to step S318, and the execution of the monitoring program 370 is ended. On the other hand, when the calculation result or the predicted calculation result of the measured SAR value in step S314 exceed the specified SAR value, the signal processing system 60 executes step S320 and then executes step S318 to end the execution of the monitoring program 370. The monitoring program 370 is repeatedly executed at very short periods by the system software 350. Accordingly, the calculation in step S314 is repeatedly performed, and monitoring regarding whether or not the measured SAR of the calculation result exceeds the specified SAR value is repeatedly performed in step S316. Therefore, in the earlier phase, it is possible to determine whether or not the measured SAR exceeds the specified SAR value.

[Database Used in the Calculation of a Predicted SAR Value or a Measured SAR Value]

Figure 6:
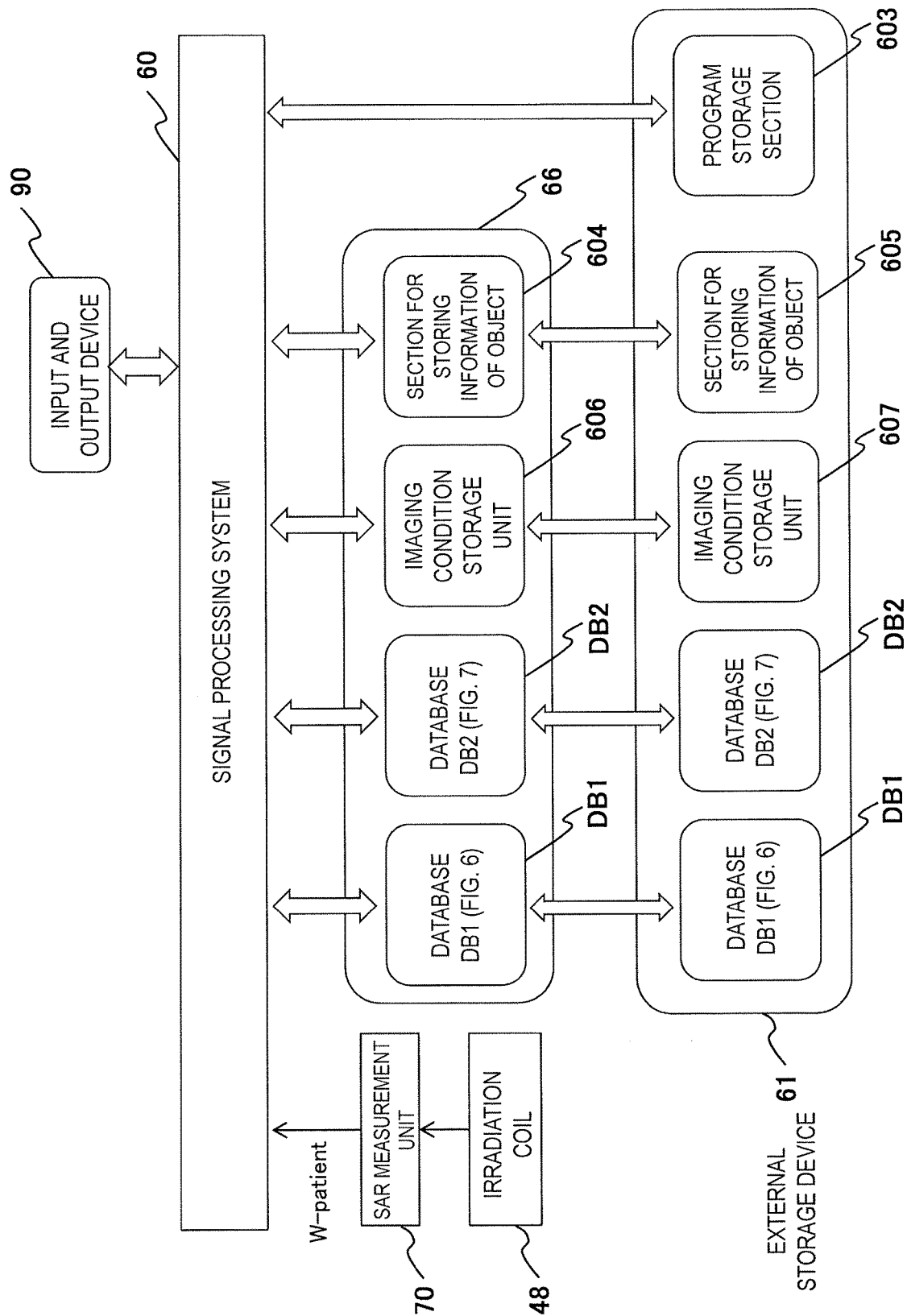
FIG. 6 is an explanatory diagram showing the storage state of information relevant to the calculation of a predicted SAR value or the calculation of a measured SAR value.

Next, the calculation of the predicted SAR described in step S134 of FIG. 3 or the calculation of the measured SAR value described in step S312 of FIGS. 4 and 5 will be described. FIG. 6 is a block diagram showing the storage state of information relevant to the calculation of the predicted SAR value or the calculation of the measured SAR value. The external storage device 61 stores information including various databases required for the imaging operation of the MRI apparatus 100. Object information and various kinds of information used as imaging conditions are transmitted from the external storage device 61, when necessary, to the internal memory 66. However, even if the above information is not transmitted to the memory 66 in particular, reading or writing may be performed for the external storage device 61. However, as an example, the following explanation will be given on the assumption that the related information is transmitted to the internal memory 66.

The internal memory 66 acquires various databases related to the object 1, software, or other pieces of information from the external storage device 61 and stores them, and writes and stores the stored information, databases, or the like into the external storage device 61 when necessary. Examples of the database include a database DB1 of W-basic shown in FIG. 7, which is data of the statistical average value of the SAR absorption rate when emitting the RF pulse, and a database DB2 of W-patient shown in FIG. 8, which is a database of the measured SAR absorption rate that is calculated by measurement by the SAR measurement unit 70 based on the RF pulse that is actually emitted to the object 1.

The major feature of the database DB1 shown in FIG. 7 or the database DB2 shown in FIG. 8 is that the W-basic or the W-patient that is data includes data corresponding to each part or each stop position of the bed 82 for imaging. The database DB1 shown in FIG. 7 includes an item of part information 610, an item of bed position information 612 that is the stop position of the bed at which the movement of the top plate 84 is stopped for imaging, an item of W-basic information 614 indicating the SAR absorption rate of the average person, and an item of head absorption rate Rh information 616 indicating the SAR absorption rate of the head of the average person.

Data Wbb1 to Wbb13 of the W-basic information 614 shown in FIG. 7, which is data of the statistical average value of the SAR absorption rate, is stored corresponding to each part or each stop position of the bed 82 for imaging. The data Wbb1 to Wbb13 is values that are calculated, as average values of the measurement values of the SAR absorption rate corresponding to each part or the stop position of the bed 82 for imaging, based on the measurement of many standard people. Bed positions L1 to L13 indicating the stop position of the bed 82 are values obtained by averaging the measured values of the bed position of each person. Therefore, when using the data Wbb1 to Wbb13, proportional calculation based on the personal height of the object 1 to be imaged is performed, and the data of the bed positions L1 to L13 is used after being converted into a value matching the physique of the individual object 1. From the database DB1, the W-basic information 614 can be searched for with the part information 610 or the bed position information 612 as a search parameter of the database DB1. In addition, the head absorption rate Rh information 616 is average data of the absorption rate Rh when the high frequency energy of the RF pulse is absorbed by the head corresponding to each stop position of the bed 82, and can be similarly read by search using the part information 610 or the bed position information 612 as a search parameter.

In the present embodiment, the data Wbb 1 to Wbb 13 that forms the W-basic information 614 is stored as a value corresponding to each part or each bed position. When the W-basic information 614 is set as data for a wide region instead of data corresponding to each part or each bed position, the error becomes very large. In the measurement results of the inventors, the values of the data Wbb1 to Wbb13 corresponding to each part or each stop position are significantly different according to the part or the bed position. When pieces of data in which parts or the stop positions of the bed 82 are different are compared with each other, there may be a severalfold difference between the values.

For this reason, in the case of using the SAR value that is calculated using the average SAR value corresponding to the wide region for which a part or the stop position of the bed 82 is not specified, it can be considered to have a very large error depending on the imaging position. When using the SAR value with large error, it is necessary to set a very large safety margin when determining the imaging conditions using the predicted SAR value obtained by calculation. Accordingly, it is difficult to set the appropriate RF pulse output. In addition, a possibility increases that an abnormal situation, in which the SAR value exceeds the specified value during the actual imaging, will occur and the imaging should be stopped.

The database DB2 shown in FIG. 8 includes part information 620 for storing the data of a part to be imaged, bed position information 622 that is the stop position of a bed to be imaged, W-patient information 624 that is data of the SAR absorption rate measured corresponding to the bed position, and head absorption rate Rh information 626 that is data of the SAR absorption rate measured for the head of the object 1.

Data Wp1 to Wp13 of the W-patient shown in FIG. 8, which is data of the SAR absorption rate measured for the object 1, is provided corresponding to each part or each stop position of the bed 82 for imaging, as in the case shown in FIG. 7. The data Wp1 to Wp13 is the values of the SAR absorption rate unique to the object 1, which have been measured by the SAR measurement unit 70 by actually emitting RF pulses from the irradiation coil 48 in each part or the stop position of the bed 82 for imaging. Bed positions L1 to L13 indicating the stop position of the bed 82 are values of the stop position of the bed 82 for a standard person. Therefore, when using the data Wp1 to Wp13, proportional calculation based on the height of the object 1 to be used is performed, data of the bed positions L1 to L13 matching the physique of the object 1 is calculated, and the calculation result is used. However, in the database DB2 described in FIG. 8, values unique to the object 1 to be imaged may be set as the values of the bed positions L1 to L13, instead of the average value. In addition, for the head, data of the absorption rate Rh at which the high frequency energy of RF pulses is absorbed into the head is stored corresponding to each stop position of the bed 82.

The internal memory 66 further includes an imaging condition storage section 606 and an object information storage section 604 regarding the object 1, and imaging conditions that are input and set are stored in the imaging condition storage section 606. Personal information, such as the stored name, or information regarding the body, such as weight or height, is stored in the object information storage section 604 regarding the object 1. Imaging conditions stored in the internal memory 66 are further stored in an imaging condition storage section 607 of the external storage device 61, and object information regarding the object 1 is stored in an object information storage section 605 of the external storage device 61 when necessary. The database DB1 or DB2 is stored in the external storage device 61. When data is modified, added, or newly created in the internal memory 66, the data is stored after being written into the external storage device 61 from the internal memory 66 when necessary. In addition, in the external storage device 61, necessary programs are stored, and programs for executing the flowcharts described in this specification are also stored.

[Calculation of the Predicted SAR Value]

The details of step 134 described in FIG. 3 will be described with reference to the flowchart in FIG. 9. This flowchart shows an operation performed by the signal processing system 60. In step S412, the signal processing system 60 calculates the energy Power seq (W) of RF pulses emitted by the irradiation coil 48 based on the imaging conditions that are input and stored in the imaging condition storage section 606 of the internal memory 66. Then, in step S414, W-basic for entire body SAR that is a standard value stored in the database DB1 is searched for with a part or the bed position L as a search parameter. Even if the same value is used for W-basic for entire body SAR, W-basic for part SAR, and W-basic for head SAR without the above-described detailed division into the W-basic for entire body SAR, the W-basic for part SAR, and the W-basic for head SAR, it is possible to obtain the predicted SAR value. However, since it is possible to read the W-basic for entire body SAR, the W-basic for part SAR, and the W-basic for head SAR based on a part or the movement stop position of the bed 82 herein, it is possible to calculate the predicted SAR value with very high accuracy.

Here, a representative example of searching for the W-basic corresponding to (Equation 1), (Equation 2), or (Equation 3) and using it will be described. In step S416, the weight W of the object 1 input in step S 102 in FIG. 3 is read from information 604 regarding the object 1 in the internal memory 66. In step S418, the operation of the above-described (Equation 1) is performed, and the value of the predicted entire body SAR (W/kg) is obtained by calculation. Thus, the signal processing system 60 calculates the predicted entire body SAR (W/kg) through steps S412 to S418. The calculated predicted entire body SAR (W/kg) is displayed in the SAR value display portion 840 shown in FIG. 2 and is stored in the imaging condition storage section 606 of the internal memory 66 in step S418.

Similarly, in step S422, W-basic for SAR of a part or the bed position to be imaged is searched for from the database DB1 with the part or the bed position as a search parameter. In addition, the mass mp of the part to be imaged is calculated from the weight of the object 1. In step S426, the operation of (Equation 2) is performed, and the signal processing system 60 calculates the predicted body part SAR. Steps S422 to S426 are a procedure executed in order that the signal processing system 60 calculates the predicted body part SAR, and the calculation result is displayed in the SAR value display portion 840 and is stored in the imaging condition storage section 606 of the internal memory 66.

A predicted head SAR value is calculated by the execution of steps S432 to S438 by the signal processing system 60, and the calculation result is displayed and stored. First, in step S432, the W-basic for head stored in the database DB1 is obtained by search with a part or the bed position as a search parameter. In step S434, the mass mh of the head is calculated from the input weight W. In addition, the head absorption rate Rh is obtained by searching from the database DB1 with the part or the bed position as a search parameter, and the operation of (Equation 3) is performed in step S438. The predicted head SAR is obtained by this calculation, and is displayed in the SAR value display portion 840 shown in FIG. 2 and is stored in the imaging condition storage section 606 of the internal memory 66 shown in FIG. 8.

Figure 9:
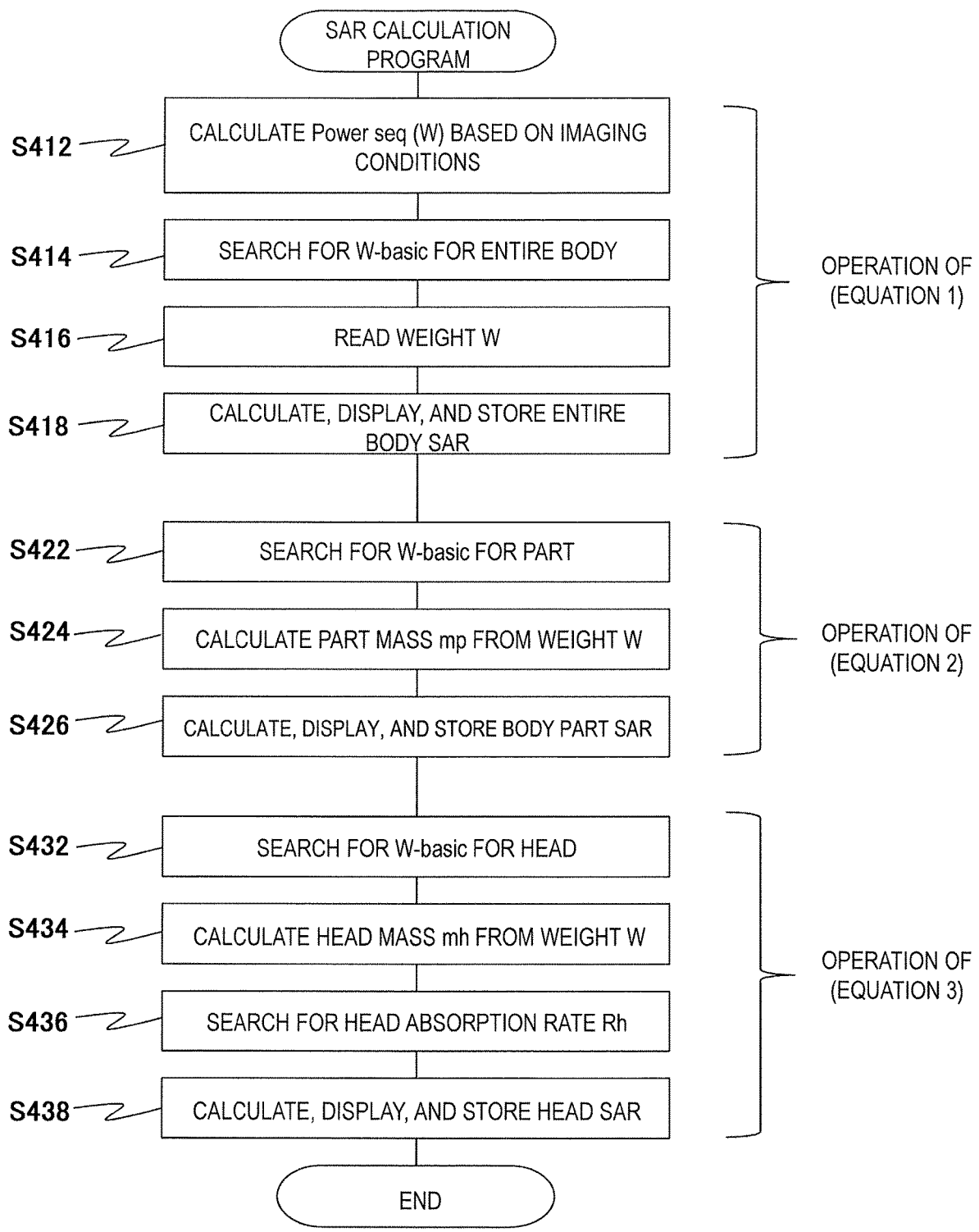
FIG. 9 is a flowchart for calculating the predicted SAR value.

By executing the flowchart shown in FIG. 9 in this manner by the signal processing system 60, the operation of (Equation 1), (Equation 2), or (Equation 3) is performed. The calculation result is displayed as the SAR value 842 in the SAR value display portion 840 shown in FIG. 2. The signal processing system 60 determines whether or not the SAR value 842 exceeds the specified SAR value 844 by executing step S136 in FIG. 3. The subsequent operation of the signal processing system 60 is the same as described with reference to FIG. 3.

[Calculation of the Measured SAR Value Using Measured W-patient]

The details of step S314 described in FIG. 4 or 5 will be described below. The SAR measurement unit 70 measures the energy absorption state of RF pulses that are high frequency pulses that have been emitted from the irradiation coil 48, calculates the absorption rate W-patient actually absorbed into the object 1 based on the measurement value, and stores it as the database DB2. Corresponding to each part or corresponding to each movement stop position of the bed 82, as described in FIG. 7, data of the W-patient based on the measurement value is stored in the internal memory 66 as the database DB2, and is further stored, for example, in the magnetic disc 64 or the optical disc 62 that is an external storage device. In the present embodiment, not only does the value of the W-patient correspond to a part, but also data of the W-patient measured corresponding to each stop position when moving the bed position is stored since the scan position differs in each part. Therefore, there is an effect that the more accurate measured SAR value is obtained.

The operation when the signal processing system 60 calculates a measured SAR value by executing step S314 described in FIG. 4 or step 314 described in FIG. 5 will be specifically described with reference to FIG. 10. Here, equations for calculating the measured SAR value based on measurement are expressed as (Equation 4), (Equation 5), and (Equation 6).

$$\text{Measured entire body } SAR(W/kg) = W-\text{patient}\frac{Powerseq(W)}{\text{object weight } M(kg)} \qquad \text{[Equation 4]}$$

$$\text{Measured body part } SAR(W/kg) = \frac{W-\text{patient}}{\text{Power } seq(W)} \quad \text{[Equation 5]}$$
$$\text{part mass of body in irradiation range } m_p \text{ (kg)}$$

$$\text{Measured head } SAR(W/kg) = \quad \text{[Equation 6]}$$
$$W - \text{patient} \frac{\text{Power } seq(W)}{\text{head mass } m_h(\text{kg})} \times R_h$$

Here, the W-patient is an absorption rate obtained by the calculation of the SAR measurement unit 70 from the measurement value described above. Power seq (W), part mass mp, head mass mh, and head absorption rate Rh are approximately the same as described in (Equation 1), (Equation 2), or (Equation 3).

Figure 10:
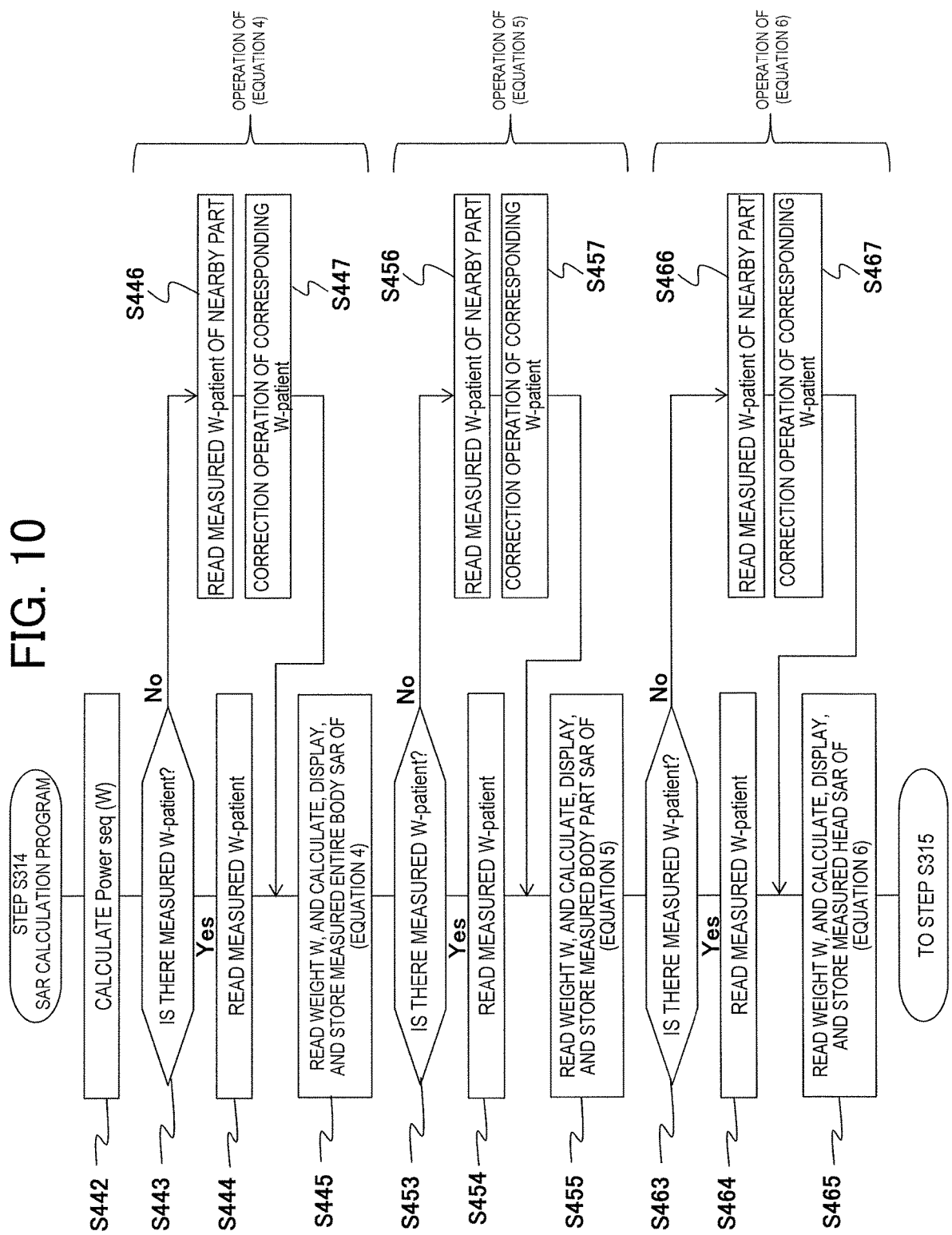
FIG. 10 is a flowchart for calculating the measured SAR value.

In the flowchart shown in FIG. 10, in step S442, the signal processing system 60 reads imaging conditions that are previously input and stored in the imaging condition storage section 606, and calculates the energy Power seq (W) of RF pulses emitted by the irradiation coil 48 based on the imaging conditions. When the Power seq (W) previously calculated by the execution of the flowchart shown in FIG. 3 or the like is stored, it is possible to use the result.

Steps S443 to S445 are a flowchart for performing the operation of (Equation 4). In step S443, for a part for which a measured SAR value is to be calculated, it is checked whether or not the W-patient, which is the absorption rate of RF pulses that is calculated based on the measurement value, is stored. When the W-patient based on the measurement is present in the database DB2, the W-patient is read from the database DB2 by search in step S444, and is used for the operation of (Equation 4). As shown in FIG. 7, the W-patient based on the measurement can be searched for with a part as a search parameter or with the bed position L, that is, a position where the object 1 is placed as a search parameter. In the present embodiment, since the W-patient based on the measurement is stored with not only a part but also the bed position L as a search parameter, it is possible to store the W-patient suitable for an imaging part. In addition, since it is possible to use the W-patient having the bed position L as a search parameter, it is possible to improve the calculation accuracy of the measured SAR value.

Therefore, the margin of the imaging conditions can be appropriately set. As a result, since the appropriate imaging conditions, especially, the irradiation energy of RF pulses can be appropriately set, the quality of a captured image is further improved.

When the W-patient of the target part or the bed position has not been measured, that is, when the corresponding W-patient has not yet finished the database DB2, the W-patient of a part near the target part or a bed position near the target bed position is read by search in step S446. Although the read W-patient is a value for the different part or the different bed position L, it is possible to consider an individual difference for the standard value of the object 1 by using the read W-patient as it is. Therefore, the accuracy of the predicted SAR value is further improved by using the measured SAR value obtained by calculation. In addition, it is possible to further improve the accuracy by correcting the value of the different part or the W-patient for the different bed position L in step S447 instead of using the value of the different part or the W-patient for the different bed position L as it is and using the corrected W-patient.

In step S445, the signal processing system 60 performs the operation of the equation shown in (Equation 4) using the W-patient calculated in step S444, or the W-patient calculated in step S446, or the W-patient corrected in step S447, displays the calculation result of the measured entire body SAR in the SAR value display portion 840 shown in FIG. 2 as the SAR value 842, and stores the calculation result of the measured entire body SAR in the imaging condition storage section 606 of the internal memory 66.

Steps S453 to S455 are a flowchart for performing the operation of (Equation 5). In step S453, in the same manner as in step S443, it is checked whether or not the W-patient for a current target part or bed position is stored. When the W-patient is present in the database DB2, the W-patient based on the measurement is read by search from the database DB2 with the part or the bed position as a search parameter in step S454. When the W-patient is not yet present in the database DB2, W-patient of a part near the target part or W-patient of a stop position near the stop position of the target bed is read by search in step S456. Using the read W-patient as it is, the measured body part SAR may be calculated in step S455. In addition, it is possible to improve the accuracy by correcting and using the W-patient of the different part or the different bed position, which has been acquired in step S456, in step S457, instead of using the W-patient of the different part or the different bed position as it is.

In step S455, the signal processing system 60 calculates the measured body part SAR by performing the operation of the equation shown in (Equation 5) using the W-patient calculated in step S454, or the W-patient calculated in step S456, or the W-patient corrected in step S457, displays the calculation result in the SAR value display portion 840 shown in FIG. 2 as the SAR value 842, and stores the calculation result in the imaging condition storage section 606 of the internal memory 66.

Steps S463 to S465 are a flowchart for performing the operation of (Equation 6). In step S463, in the same manner as in step S443, it is checked whether or not the W-patient for a current target part or bed position is stored. When the W-patient is present in the database DB2, the W-patient based on the measurement is read by search from the database DB2 with the part or the bed position as a search parameter in step S464. When the W-patient is not present in the database DB2, W-patient of a part near the target part or W-patient of a bed position near as the target bed position is read by search in step S466. Using the read W-patient as it is, the measured head SAR may be calculated in step S465.

In addition, the W-patient of the different part or the W-patient for the different bed position that has been acquired in step S466 is corrected in step S467, instead of using the W-patient of the different part or the W-patient for the different bed position as it is. By correcting the W-patient of the different part or the W-patient for the different bed position as described above, it is possible to obtain the measured head SAR value with higher accuracy than when using the W-patient of the different part or the W-patient for the different bed position as it is.

In step S465, the signal processing system 60 calculates the measured head SAR by performing the operation of the equation shown in (Equation 6) using the W-patient calculated in step S464, or the W-patient calculated in step S466, or the W-patient corrected in step S467, displays the calculation result in the SAR value display portion 840 shown in FIG. 2 as the SAR value 842, and stores the calculation result in the imaging condition storage section 606 of the internal memory 66.

The flowchart shown in FIG. 10 is the details of step 314 described in FIG. 4 or step 314 described in FIG. 5, which is executed by the signal processing system 60. After the execution of FIG. 10, the signal processing system 60 executes step S316 shown in FIG. 4 or 5 to determine whether or not each calculation result exceeds the specified SAR value as described above. Specific explanation is the same as described above, and will be omitted. In the present embodiment, after performing all of the operations of (Equation 4), (Equation 5), and (Equation 6), it is determined whether or not the value of measured SAR that is the calculation result exceeds the specified SAR value in step S316. However, whenever the operation of (Equation 4), (Equation 5), or (Equation 6) is separately completed, comparison between the value of the measured SAR that is the calculation result and the corresponding specified value, which is the processing of step S316 shown in FIG. 4 or 5, may be performed.

[Other Embodiments Regarding the Imaging Conditions Based on Monitoring Using the Measured SAR Value in FIG. 4]

In FIG. 3, a predicted SAR value is calculated to prevent the SAR value from exceeding the specified value in the actual imaging operation based on the set imaging schedule including the imaging conditions. If a situation in which the specified value is exceeded occurs or if it is predicted to exceed the specified value, the imaging is stopped in step S320 in the flowchart described in FIG. 4. However, the imaging of the MRI in the target part or the bed stop position is required for the object 1, and it is not possible to stop the imaging in many cases. Therefore, it is desirable to reset the imaging conditions appropriately and to resume the imaging in many cases. In this case, the operator changes the imaging schedule including the imaging conditions to perform imaging further. An embodiment for this is shown in FIG. 11.

There is an individual difference in the energy absorption rate W-patient unique to the object 1. Accordingly, the energy absorption rate W-patient unique to the object 1 may be greatly different from the standard energy absorption rate W-basic for some people. By using the W-patient calculated based on the measurement value by the SAR measurement unit 70 as described in FIG. 4, it is possible to respond to the above case even if the individual difference is large. Therefore, it is possible to improve the calculation accuracy of the SAR value. By performing the SAR calculation based on the imaging conditions using the W-patient and then performing measured SAR calculation along the imaging schedule of other parts using the W-patient of the part already measured, it is possible to reduce a lowering in the accuracy of the SAR due to individual differences.

Using the W-patient for a part already measured as described above, subsequent predictive calculation of the measured SAR value along the imaging schedule can be performed to some extent. Thus, predictive calculation of the measured SAR of other parts that have not yet been measured is performed by using the W-patient already obtained by measurement, and it is determined whether or not the specified SAR value is exceeded based on the calculation result (hereinafter, referred to as a predicted value of the measured SAR). When the specified SAR value is exceeded, it is desirable that the signal processing system 60 outputs the situation through a display means or the like to prompt the operator to change the imaging schedule including the imaging conditions. An embodiment for this is shown in FIG. 11.

Figure 11:
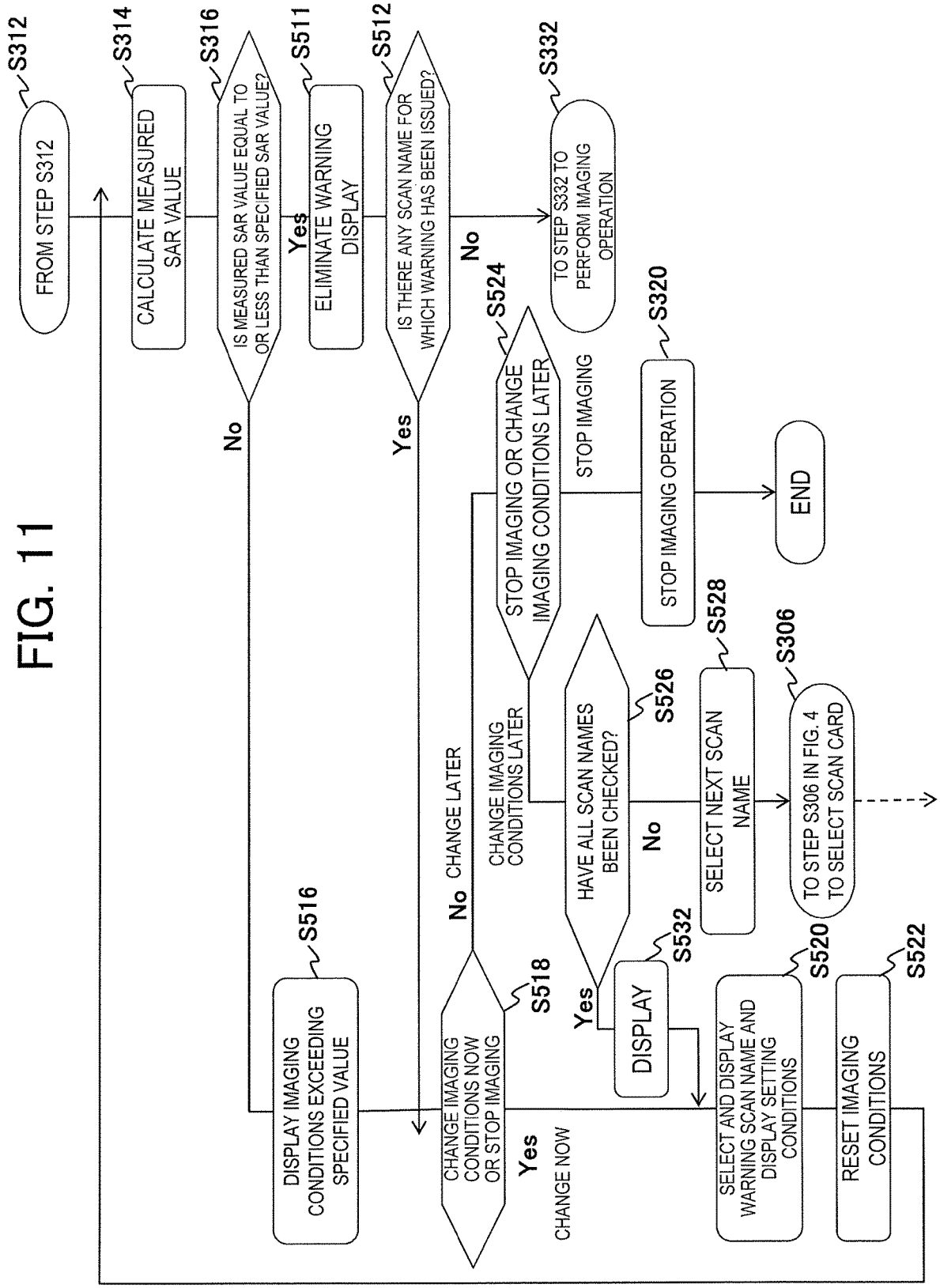
FIG. 11 is a flowchart showing still another embodiment of the flowchart of the imaging operation shown in FIG. 4.

FIG. 11 is obtained by adding a new step to the flowchart described in FIG. 4. In particular, a new step is added between step S316 and step S332 or S320. Since the other steps described in FIG. 4 are approximately the same as already described, explanation of these steps will be omitted.

In FIG. 11, steps S302 to S308 described in FIG. 4 are executed, and then step S312 is executed. After step S312, step S314 is executed. Using the W-patient stored in the database DB2 that has been calculated by the SAR measurement unit 70, the operation of the measured SAR value based on (Equation 4), (Equation 5), or (Equation 6) is performed in step S314. When the measured SAR value that is the calculation result is equal to or less than the specified SAR value, as in FIG. 4, the signal processing system 60 executes step S511 or S512 from step S316, and proceeds to step S332.

However, when there is a warning display of the warning 846 or the warning column 848 for the scan name 152 for which the determination in step S316 has been made, the warning display of the warning 846 or the warning column 848 is eliminated in step S511 since it has been confirmed that the cause of the previously issued warning is solved by the determination in step S316. When a warning has been issued for another scan name 152, it is necessary to perform an imaging operation after removing the scan name 152 for which a warning has been issued by resetting the imaging conditions of the scan name 152 for which a warning has been issued.

For this reason, in step S512, it is determined whether or not there is any scan name 152 for which a warning has been issued. When there is no scan name for which a warning has been issued, the execution of the signal processing system 60 proceeds to step S332. When there is another scan name for which a warning has been issued, display for asking the operator whether to immediately change the imaging conditions of the scan name 152 for which a warning has been issued or to change the imaging conditions later is performed in step S518. Based on the determination of the operator, it is determined whether to execute step S520 or to execute step S524. The details of the operation in step S511 or S518 or the purpose of the operation will be described later.

On the other hand, when the measured SAR value that is a calculation result exceeds the specified SAR value, the execution of the signal processing system 60 proceeds to step S516 to display the warning 846 in the SAR value display portion 840 shown in FIG. 2 and display the scan name in the warning column 848 of the scan list display portion 810. The display of the warning 846 is a display corresponding to the selected scan name 152. If the operator forcibly selects the next scan name in order to check the state of warning for all of the scan names 152 displayed in the list of the scan list display portion 810 or if the operator selects to postpone responding to the warning as will be described below, the execution of the signal processing system 60 proceeds to processing for the new scan name.

In this case, the display of the imaging condition display portion 820 is changed to the display of the state of the newly selected scan name 152. As a result, the display of the warning 846 for the previous scan name 152 disappears, and the display of the warning 846 is performed according to the state of the new scan name 152. On the other hand, the warning column 848 is the display of warning states for all scan names of the list of scan names described in the scan list display portion 810, and the warning display of the warning column 848 is not changed even if the scan name 152 to be selected is changed. For example, in a state in which the measured SAR value exceeds the specified SAR value in a plurality of scan names 152, the plurality of scan names that are warning targets are displayed in the warning column 848. Although the plurality of scan names that are warning targets are displayed in the scan list display portion 810 in the present embodiment, the warning column 848 may be displayed in another location. It is very important to notify the operator for which scan name 152 a warning has been issued. By displaying the scan name as a warning target that does not satisfy the conditions of the SAR as described above, it is possible to prevent the response error in setting the imaging conditions. Therefore, there is a large effect in terms of the improvement in reliability or safety.

The execution of the signal processing system 60 proceeds from step S316 to step S516 to display a warning in the SAR value display portion 840 or the warning column 848, and proceeds from step S516 to step S518. Alternatively, when there is a scan name for which a warning has been issued in step S512, step S518 is executed. In step S518, display for asking the operator whether to immediately respond to the cause of the warning or to postpone the response including the stopping of the imaging is performed, and the instruction of the operator is awaited. For example, a case can be considered in which a response is determined after checking the presence of a warning for all of the scan names described in the scan list display portion 810. In this case, the operator inputs an instruction of the corresponding content later. According to the instruction of the operator, the signal processing system 60 executes step S524. The position where there is a display for the checking of the operator, which is performed in step S518, is not particularly specified. However, it is easy to perform determination if the display is performed near the warning column 848, for example. In addition, various display formats can be used, and there is no need to define a format in particular.

When the operator inputs an instruction to immediately change the imaging conditions for the display in step S518, the execution of the signal processing system 60 proceeds from step S518 to step S520 according to the instruction, and the scan name for which a warning has been issued is automatically selected in step S520. In addition, the scan position 834 or the scan position 836 of the selected scan name is displayed in the positioning image display portion 830, and the imaging conditions including the previously set imaging parameters that caused the warning are displayed in the imaging parameter display portion 850. In the SAR value 842 of the SAR value display portion 840, the measured SAR value that caused the warning is displayed. In addition, the corresponding specified SAR value 844 is displayed.

When the imaging conditions including new imaging parameters for changing the conditions of the positioning image display portion 830 or the imaging parameter display portion 850 are input in step S522, step S314 is executed again. The calculation of the measured SAR value based on the W-patient is performed by (Equation 4), (Equation 5), or (Equation 6) using the newly input information, and step S316 is executed again. Thus, by calculating the measured entire body SAR value, the measured body part SAR value, or the measured head SAR value using (Equation 4) to (Equation 6) described above using the W-patient obtained by the measurement and calculation of the SAR measurement unit 70, it is determined whether or not the SAR conditions are satisfied. In this manner, the optimal imaging conditions are set.

On the other hand, when the imaging conditions for the warning are not changed immediately, for example, when the presence of a warning is also checked for the imaging conditions of other scan names and then the imaging conditions are changed or the imaging operation itself is stopped in step S518, the operator inputs an instruction of "NO" for the display based on step S518. According to this instruction, it is selected whether to change the imaging conditions later or to stop the imaging operation in step S518, and the execution proceeds to step S524. In step S524, display for asking about whether to simply stop the imaging operation or to check the presence of a warning for other scan names first is performed. When the operator inputs an instruction to stop the imaging, the execution proceeds to step S320 as described in FIG. 4. In step S320, the signal processing system 60 performs processing for stopping the imaging operation, so that the imaging control is ended.

In step S524, when "imaging conditions will be changed later" is selected for purposes for determining the presence of a warning for other scan names first and the like, the execution of the signal processing system 60 proceeds to steps S526 and S528. In step S528, the next scan name of the scan names 152 displayed in the scan list display portion 810 is selected, and step S306 in FIG. 4 is executed. Therefore, it is possible to check the presence of a warning in order for all of the scan names 152 in the scan list display portion 810. When the presence of a warning has been checked in order for the scan names 152 in the scan list display portion 810 and the checking of all scan names in the scan list has been completed, the completion of the checking of all of the scan names is determined in step S526, and the execution of the signal processing system 60 proceeds to step S532. Display meaning the completion of the checking of all of the scan names is performed in step S 532, and the change of the imaging conditions is started for the scan name for which a warning has been issued in step S520.

For example, considering a case in which the warning has been issued for the first scan A 152 in the scan list displayed in the scan list display portion 810, the execution of the signal processing system 60 proceeds from step S316 to step S518 through step S516. As described above, in step S516, the scan name in the warning 846 or the warning column 848 is displayed. When the instruction of NO is given by the operator in step S518, step S524 is executed, and steps S526 to S528 are further executed. In step S528, a scan B 152 that is the next scan name in the scan list is selected. In the scan B, even if no warning is issued, the execution proceeds from step S512 to step S518, step S528 is executed through steps S524 and S526, and a scan C 152 that is the next scan name 152 is selected. When there is a warning for the selected scan name, the scan name is displayed in the warning 846 or the warning column 848 in step S316. Then, through steps S316 to S518, steps S524 to S526 are executed and step S528 is executed, and the selected scan names are updated in order. Even if there is no selected scan name for which a warning has been issued, the scan names 152 selected in step S528 are updated in order through steps S512 to S518. It is possible to check the presence of a warning for all of the scan names 152 up to a scan E 152 that is the last scan name 152. For all of the scan names 152 for which a warning has been issued, step S516 is executed, and the relevant scan names 152 are displayed in order in the warning column 848. Therefore, results of the checking of the presence of a warning for all of the scan names are displayed in the warning column 848. The operator can understand the overall situation by observing the warning column 848. Thus, by understanding the overall situation, it is possible to determine which measurement conditions are to be set. This is helpful when the state of the object 1 is very different from that of the standard person.

When the occurrence of a warning for the SAR is avoided by resetting the imaging conditions in step S520 after checking the presence of a warning for all of the scan names 152 in the scan list displayed in the scan list display portion 810, step S511 is executed after the determination of "YES"

in step S316, in which the scan name displayed in the warning 846 or the warning column 848 is eliminated. As a result, the operator can check the situation of the presence of a warning due to the resetting of the imaging conditions by observing the warning column 848.

When there is a scan name for which a warning is not avoided other than the scan name for which a warning has been avoided by resetting the imaging conditions, the execution of the signal processing system 60 proceeds to step S518 based on the determination in step S512, and proceeds from step S518 to step S520. In step S520, scan names for which a warning has been issued are selected in order. After the selection of the scan name in step S520, resetting of the imaging conditions is performed in step S522. When it is confirmed that the warning state has been improved and the warning state has been avoided in step S316 based on the calculation result in step S314, the execution proceeds from step S316 to step S511. In step S511, scan names displayed in the warning column 848 are eliminated. In this manner, when the number of scan names for which a warning has been issued is reduced in order and the resetting of the imaging conditions is performed for all of the scan names for which a warning has been issued so that the warning state of all of the scan names is avoided, the execution proceeds from step S512 to step S332. In step S332, the imaging operation is started. Subsequent operation is the same as described in FIG. 4.

Even if the operator has input NO in step S518, the execution proceeds from step S524 to step S526 and to step S532. In step S532, display showing that determination regarding the presence of a warning has been made for all of the scan names is performed, and step S520 is executed. However, when the operator wants to stop the imaging operation, the execution proceeds from step S524 to step S320 to stop the imaging operation.

Even if there is a possibility that the measured SAR value will exceed the specified value since the state of the object 1 to be imaged is greatly different from the W-basic that is standard data shown in FIG. 7, it is possible to quickly respond to this situation through the operation shown in FIG. 11.

[Relationship Between a Standard Bed Position and a Bed Position Unique to the Object 1]

In the present embodiment, a part that is an object to be imaged and a bed position are used as search parameters in the database DB1 or the database DB2 shown in FIG. 7 or 8. Also in the column of the imaging parameter display portion 850 described in FIG. 2, there is an input column and a display column of the bed position, so that the bed position 856 is displayed. The bed position that is input or displayed in this column is used for position control for the imaging of the object 1. The bed position shown in FIG. 7 or 8 and the bed position that is input or displayed in the imaging parameter display portion 850 may be a bed position for a standard person, or may be a bed position corresponding to the individual object 1.

However, it takes time to specifically measure the position of each part corresponding to each object 1, and this is not so efficient. In addition, as search parameters of the database DB1 or the database DB2, search parameters that can be normally used for a lot of people are convenient in terms of many points. For this reason, the bed position is treated in the dimensional relationship with respect to the standard person. In addition, when the signal processing system 60 actually moves the top plate 84 of the bed 82 through the bed control device 80 or and performs the specific control, the bed position for the standard person is used after being converted into a bed position corresponding to the individual object 1 using the data obtained from the height, weight and the scanogram described in FIG. 3, which are the input personal data of the object 1. Instead of the data of the bed position for the standard person, personal data obtained by measuring the position of a part of the individual object 1 may be also be used for input and display. Alternatively, both the standard bed position data and the individual bed position data may be used, so that the operator can use these pieces of data selectively.

[Embodiment in Which W-patient is Used Instead of W-basic]

The embodiment for setting the imaging conditions satisfying the specified SAR value based on the predicted SAR value using the W-basic, which is the data of the standard SAR absorption rate, has been described previously with reference to the flowchart described in FIG. 3. However, instead of the W-basic that is the data of the standard SAR absorption rate, W-patient that is the personal SAR absorption rate of a person for whom imaging is scheduled.

An embodiment in which the imaging conditions satisfying the specified SAR value are set by calculating the measured SAR using the W-patient that is the personal SAR absorption rate of a person for whom imaging is scheduled will be described with reference to FIG. 12.

In the embodiment shown in FIG. 3, it is determined whether or not the set imaging conditions satisfy the specified SAR value by calculating the predicted SAR value using the W-basic, which is a standard SAR absorption rate, and comparing the predicted SAR value with the specified SAR value. There is an individual difference for whether or not the W-basic that is a standard SAR absorption rate and the W-patient that is the SAR absorption rate for the individual object 1 for whom imaging is scheduled are close values. Depending on a person, the difference may be large. The embodiment described in FIG. 12 is an embodiment in which the operations of (Equation 4), (Equation 5), and (Equation 6) are performed using the personal W-patient of the object 1 calculated by the SAR measurement unit 70 and it is determined whether or not the set imaging conditions satisfy the specified SAR value. Steps for approximately the same operations as in FIG. 3 are denoted by the same reference numerals, and repeated explanation will be avoided if possible.

Figure 12:
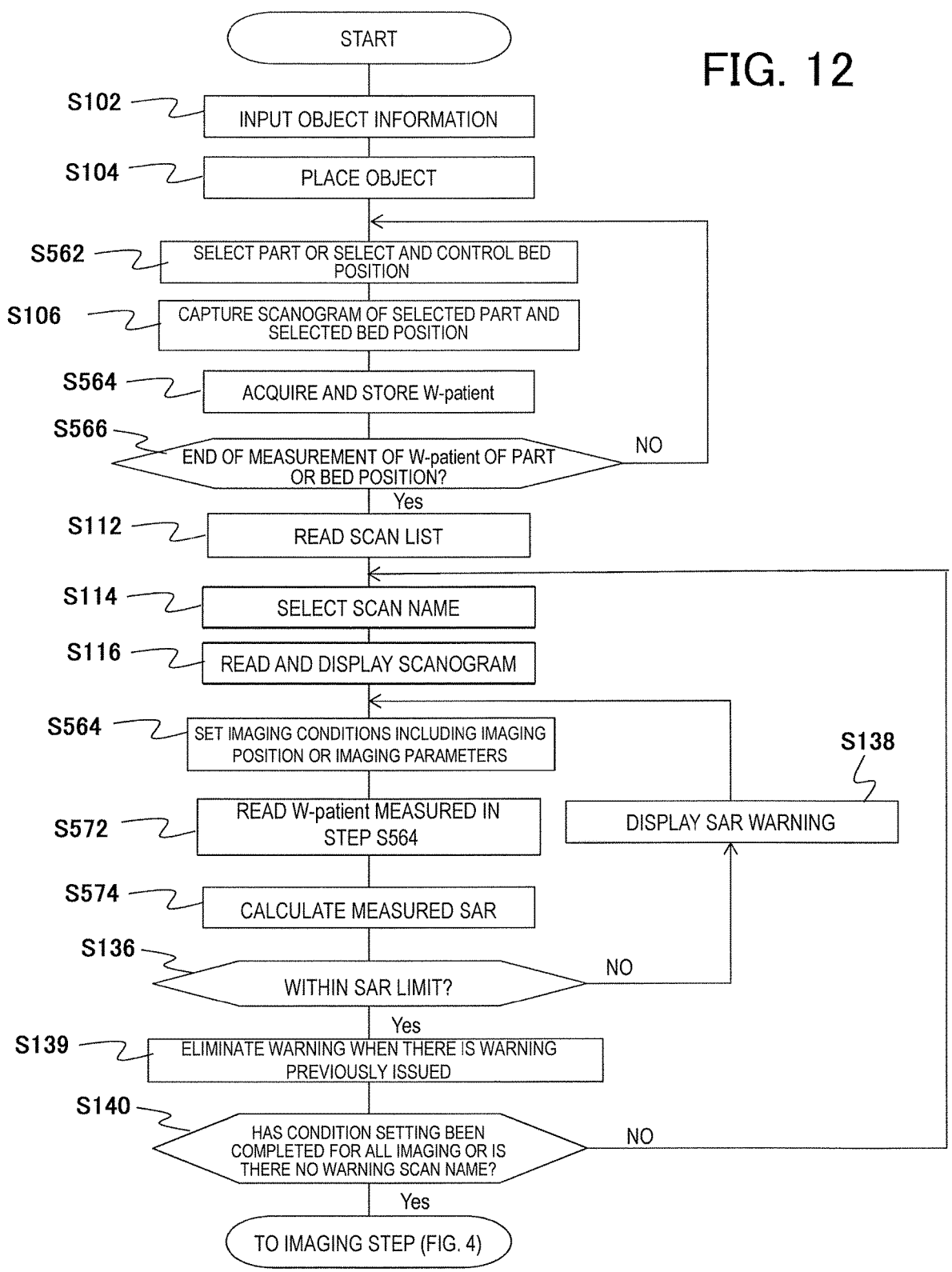
FIG. 12 is a flowchart showing still another embodiment of the embodiment shown in FIGS. 3 and 4.

When the signal processing system 60 starts the execution of the flowchart shown in FIG. 12, an examination part of the object 1 or the bed position, name, weight, height, age, and the like corresponding to the part are input based on an input image displayed by the signal processing system 60 in step S102. The signal processing system 60 assigns the scan name 152 in order corresponding to the input part or bed position, and displays the scan name 152 in the scan list display portion 810. In step S104, the object 1 is placed on the top plate 84 of the bed 82. For example, the top plate 84 is controlled, based on the signal of the marker 15, so that the reference position of the object 1 comes to the center position of the gradient magnetic field in the gantry. Therefore, it is possible to control the bed 82 according to a part or bed position data L1 to L13 so that each part of the object 1 comes to a predetermined position in the gantry. Instead of the input of a part to be imaged in step S102, it is also possible to input a bed position for specifying a part. In addition, both a part to be imaged and a bed position for specifying the scan position may be input. In this case, based on the information of the input part and the input bed position, the top plate 84 of the bed 82 is controlled through the bed control device 80.

Although the explanation of step S562 or step S566 in FIG. 12 is omitted in the explanation of FIG. 3, it is also possible to perform an operation described below in FIG. 3. In step S562, when a plurality of parts or bed positions have been previously input in step S102, one of the plurality of input parts or bed positions is selected, for example, in the order of the display of the scan list display portion 810. For example, the first scan A is specified among the scan names of the scans A to E displayed in the scan list display portion 810, and the head that is a part to be imaged of the scan A is selected. In addition, the signal processing system 60 controls the top plate 84 of the bed 82 through the bed control device 80 so that the object 1 is disposed at a position where the scanogram of the head is to be captured.

In step S106, a scanogram is captured by emitting RF pulses from the irradiation coil 48. In step S564, the SAR measurement unit 70 measures the W-patient that is the actual SAR absorption rate of the object 1. The W-patient obtained by the measurement indicates the personal SAR absorption rate of the object 1. The signal processing system 60 stores the calculated W-patient in the internal memory 66 as data of the database DB2. In this case, the search parameter for searching the database DB2 is a part or a bed position or both. Needless to say, in order to select the database DB2 corresponding to the individual object 1 from among a number of databases DB2, data specifying the object 1, for example, the name or the specific number is used. For example, in the present embodiment, it is possible to specify the database DB2 corresponding to the object 1 from a plurality of stored databases using the name and to search for and read the W-patient, which is previously stored, from the specified database DB2 with a part or the bed position as a search parameter.

It is preferable that the SAR measurement unit 70 calculates the W-patient based on the irradiation of RF pulses in the actual imaging state. On the other hand, the output of RF pulses required to capture the scanogram is smaller than the output of RF pulses in the actual imaging state. However, using the irradiation of RF pulses for capturing the scanogram, it is possible to check the state of the individual difference, which causes a difference between the W-basic that is a standard SAR absorption rate and the W-patient that is the SAR absorption rate of the individual object 1, due to calculating the W-patient. Therefore, it is possible to reduce the error based on the individual difference by using the W-patient obtained using the RF pulses for capturing the scanogram. In addition, since there is data of both the W-basic that is a standard SAR absorption rate and the W-patient that is the SAR absorption rate of the individual object 1, the value of the W-patient obtained using the RF pulses for capturing the scanogram may be corrected and used when necessary.

When there is one part or one bed position to be imaged, the signal processing system 60 determines that the capturing of the scanogram or the detection of the W-patient has ended in step S566, and the execution of the signal processing system 60 proceeds to the next step S112. When a plurality of parts or a plurality of bed positions to be imaged are present, it is determined that parts or bed positions to be processed are present in step S566, and the execution of the signal processing system 60 proceeds to step S562 again. Then, the above-described operation is repeated. In this manner, for all of the input parts or bed positions, the W-patient is measured by the SAR measurement unit 70. The value of the W-patient that the signal processing system 60 acquires from the SAR measurement unit 70 is stored with the part or the bed position as a search parameter as shown in FIG. 8, and is stored as the database DB2 in the internal memory 66. In FIG. 8, the head to the feet are described as imaging parts. In the present embodiment, however, the SAR measurement unit 70 measures the W-patient for the part or the bed position input in step S102, and the database DB2 is created from the W-patient measured by the SAR measurement unit 70.

In order to input and set the imaging conditions, a scan list is read out to the scan list display portion 810 described in FIG. 2 in step S112, and the scan name 152 in the scan list is selected in step S114. The selection is performed in display order, for example. In step S116, a scanogram relevant to the selected scan name 152 is read, and is displayed in the positioning image display portion 831. As described above, based on the display in the image display portion 831, it is possible to input the scan position 834 or the scan position 836. In step S564, the scan position 834 or the scan position 836 is input and set, and the imaging parameters are input and set. In FIG. 12, the operations of S122 or step 124 and step S132 in FIG. 3 are collectively described as step S564.

When the imaging conditions including the scan position or the imaging parameter of the scan name selected in step S114 are roughly input in step S564, processing for checking whether or not the condition that the SAR value does not exceed the specified SAR value is satisfied in the case of imaging under the input imaging conditions is performed in steps S572, S574, and S136 for the confirmation of the safety regarding the SAR. First, in step S572, the W-patient that is the data of the database DB2 that the signal processing system 60 has acquired from the SAR measurement unit 70 and stores in previous step S564 is read with the part or the bed position as a search parameter. In step S574, the measured entire body SAR, the measured part SAR, or the measured head SAR is calculated based on (Equation 4), (Equation 5), or (Equation 6) using the W-patient that is the read data. In step S574, the calculation result is displayed as the SAR value 842 in the SAR value display portion 840 of the imaging condition display portion 820 described in FIG. 2, and the specified SAR value 844 is further displayed.

In step S136, it is determined whether or not the measured entire body SAR, the measured part SAR, or the measured head SAR calculated based on (Equation 4), (Equation 5), or (Equation 6) described above is a value smaller than the specified SAR value set for each of them. When any of the three kinds of SAR values calculated as described above exceeds the specified SAR value set for each of them, "NO" is determined in step S136 and a warning is displayed in the SAR value display portion 840 or the warning column 848 in step S138. The operation in step S136 is approximately the same as step S136 described in FIG. 3 or step S316 described in FIG. 4.

After displaying the warning in the SAR value display portion 840 or the warning column 848 in step S138, the process returns to step S564 to re-input the imaging conditions including the scan position and the imaging parameter in order to lower the value of the SAR that is the cause of the warning. On the other hand, when it is determined that all of the operation values calculated based on (Equation 4), (Equation 5), or (Equation 6) do not exceed the corresponding specified SAR values in step S136, the execution proceeds from step S136 to step S139, and the relevant warning is eliminated when the warning has been issued in the SAR value display portion 840 or the warning column 848 in step S138. Then, in step S140, it is determined whether or not the input and setting of the imaging conditions have been completed for all of the scan names 152 displayed in the scan list display portion 810. When the input and setting of the imaging conditions have not been completed, the execution proceeds to step S114 in which the next described scan name 152 is selected, the above-described operation is repeated, and the imaging conditions are determined The above operation is repeated until the input and setting of the imaging conditions for all of the scan names 152 are completed. When the setting of the imaging conditions has been completed, it is determined that the setting of the imaging conditions has been completed for all of the scan names 152 in step S140, and imaging steps are executed. The imaging operation is performed based on the set imaging conditions, and specific explanation thereof will be omitted.

[Embodiment of the Setting of Imaging Schedule Considering the Imaging Time]

In the embodiment described above, it has been determined whether or not the specified value of the SAR is exceeded separately for each scan name 152 that is input and displayed in the scan list display portion 810. An embodiment described in FIG. 13 relates to a method of setting the imaging conditions satisfying the specified value of the SAR by changing a plurality of imaging operations, that is, a scan schedule. Needless to say, both the method described in FIG. 13 and the method described previously may be used together. The "concept of changing the schedule of imaging operation" used herein includes not only the concept of changing the order of imaging for scan names for which imaging is scheduled but also the concept of changing the moving speed of the bed 82 or the concept of changing the time until the RF pulses for imaging are emitted after the movement of the bed 82 is stopped.

Figure 13:
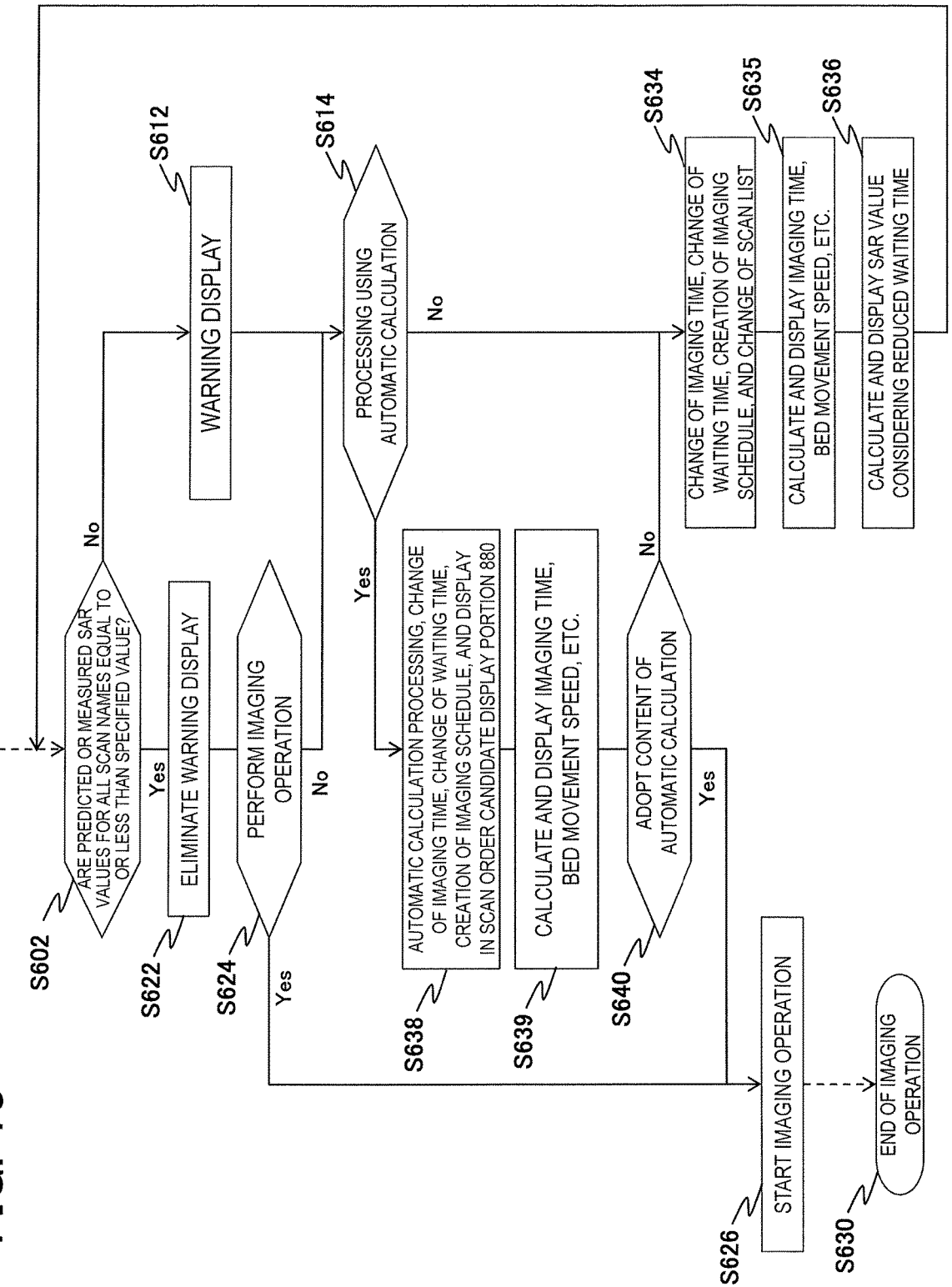
FIG. 13 is a flowchart showing still another embodiment of the embodiment shown in FIGS. 3 and 4.

In step S602 shown in FIG. 13, it is determined whether or not the specified value of the SAR is exceeded for each scan name 152 described in the scan list display portion 810. The procedure up to step S602 is the same as described in the previous embodiment. For example, step S602 includes an operation corresponding to step S316 or step S512 described in FIG. 11.

The basic idea of the response to the determination result in step S602 is that, when all of the scan names for which imaging is scheduled satisfy the conditions of the SAR, the imaging operation may be started as it is, but it is possible to change the setting of the imaging conditions, such as shortening the imaging time or increasing the output of RF pulses. On the other hand, when one or more scan names for which the conditions of the SAR are not satisfied are present in all of the scan names for which imaging is scheduled, the imaging conditions of the relevant scan name may be changed instead of responding to the case by changing only the imaging conditions of the scan name that does not meet the criteria. However, there is another method in which the time required for imaging is increased or the waiting time is set or increased so that the conditions of the SAR are also satisfied for the scan name for which the conditions of the SAR are not satisfied.

In step S602, it is determined whether the prediction state is that all of the scan names 152 described in the scan list display portion 810 is less than the specified value of the SAR and the conditions of the SAR are satisfied or that the conditions of the SAR are not satisfied on the contrary. First, it is assumed that all of the scan names 152 described in the scan list display portion 810 are less than the specified value of the SAR and accordingly it can be determined that the conditions of the SAR are satisfied. In step S622, if there is a warning that has been issued before, specifically, a warning in the warning column 848 or the warning 846, the warning is eliminated.

Then, in step S624, since the imaging operation can be started in this state, it is determined whether or not to start the imaging with the imaging conditions and imaging schedule in this state. Specifically, display for asking the operator about the determination is performed. When the operator determines that the imaging is to be started without further adjusting the imaging schedule or the like, the execution of the signal processing system 60 proceeds from step S624 to step S626 according to the operation instruction from the operator, and the imaging operation is started. Then, when the imaging ends, processing for the end of the imaging is performed in step S630. For example, when the operator selects the imaging start mark 860 described in FIG. 2, the execution of the signal processing system 60 proceeds from step S624 to step S626 to start the imaging operation.

As described above, even if the conditions of the SAR are satisfied, it is possible to increase the output of RF pulses by shortening the time required for imaging or by changing the imaging conditions. Thus, it is possible to further improve the workability or to further improve the quality of imaging. In this case, based on the operation of the operator, the execution of the signal processing system 60 proceeds from step S624 to step S614, and the imaging conditions or the imaging schedule is changed in step S634 or step S638. In step S614, it is determined whether the operator himself or herself changes the imaging conditions or the imaging schedule or the signal processing system 60 automatically makes a change proposal. When display for asking the operator is performed and the signal processing system 60 makes a change proposal automatically in step S614, the execution of the signal processing system 60 proceeds from step S614 to step S638 according to the operation instruction from the operator.

In step S638, the signal processing system 60 changes the order of the scan name list automatically, thereby changing the imaging order. The waiting time is changed according to the change of the imaging order. Alternatively, only the waiting time may be changed without changing the imaging order. The signal processing system 60 changes the waiting time or changes the imaging order so that the conditions of the SAR are satisfied. A new change result is displayed on the scan order candidate display portion 880 shown in FIG. 2. Here, the content displayed in the scan order candidate display portion 880 is approximately the same as the content displayed in the imaging schedule display portion 870 to be described below. A large difference between the content displayed in the imaging schedule display portion 870 and the content displayed in the scan order candidate display portion 880 is that the display content of the imaging schedule display portion 870 is input by the operator himself or herself in step S634 to be described below and the display content of the scan order candidate display portion 880 is automatically calculated by the signal processing system 60 in step S638.

The calculation of the imaging time, the moving speed of the bed, and the waiting time and the total calculation according to the processing of step S638 is performed in step S639, and the result is additionally displayed in the display content of the scan order candidate display portion 880. As described above, the display shown in FIG. 14 is a display of the imaging schedule display portion 870, but is basically the same as the display content of the scan order candidate display portion 880. The same content as the content obtained by the calculation in step S639 is added to the content in FIG. 14, and the display content of the scan order candidate display portion 880 in step S639 is the same as the content shown in FIG. 14. In step S640, the operator determines whether or not to start the imaging operation according to the display of the scan order candidate display portion 880 described above. The operator determines whether or not to start the imaging operation based on the display content of the scan order candidate display portion 880. When the operator starts the imaging operation, the execution of the signal processing system 60 proceeds from step S640 to step S626 according to the instruction from the operator, thereby starting the imaging operation. On the other hand, when it is necessary to change the imaging schedule or the like, the execution proceeds from step S640 to step S634 according to the instruction from the operator.

When there is a scan name that does not meet the SAR criteria in step S602, a warning is displayed in the warning 846 or the warning column 848 in step S612 of the signal processing system 60, and the execution of the signal processing system 60 proceeds to step S614. In step S614, as described above, it is determined whether the signal processing system 60 automatically responds to the situation or the operator himself or herself responds to the situation. When the operator himself or herself makes an instruction to change the imaging schedule or the like in step S614, the execution of the signal processing system 60 proceeds from step S614 to step S634. When the operator himself or herself inputs the imaging schedule or the like without accepting the change proposal obtained by the calculation of the signal processing system 60 in step S640, step S634 is executed after step S640 even if the instruction is given.

The processing of step S634 will be described with reference to FIG. 14. In step S634, not only the imaging schedule but also the imaging conditions may be changed instead of changing only the imaging schedule, or only the imaging conditions may be changed without changing the imaging schedule. The change of the imaging conditions is the same as described in the above embodiment. In the present embodiment, the change of the imaging schedule will be described.

Specifically, the change of the imaging schedule is to change the imaging order of the scan name 152 described in the scan list display portion 810 or to increase the waiting time. Although the waiting time is changed by changing the imaging order in many cases, only the waiting time may be changed without changing the imaging order. Here, the processing for the change of the waiting time includes processing for the change of the moving speed of the top plate 84 of the bed 82.

FIG. 14 shows the display content of the imaging schedule display portion 870 when the imaging order of the scan name has been changed. For example, the imaging schedule display portion 870 is provided in the setting image 800 in FIG. 2, and information regarding the order, waiting time, and the like according to the execution of the imaging schedule is displayed. An item 652 indicates an imaging order, and an item 654 indicates a scan name for which imaging is scheduled. In the present embodiment, the imaging operation of each scan name is performed according to the order described in the item 654. The order of the scan name in the item 654 is the same as the order of the scan name 152 in the scan list display portion 810 described in FIG. 2, and it is possible to change the order of imaging by changing the order of the scan name 152 in the scan list display portion 810 or by changing the order of the scan name in the item 654 in FIG. 14. When the order of the scan name is changed in one of the scan list display portion 810 and the item 654, the order of the scan name in the other one is automatically changed accordingly.

An item 656 indicates a part of an imaging target, and an item 658 indicates a bed position, that is, a stop position of the top plate 84 of the bed 82 for imaging. In the example shown in FIG. 14, the part described in the item 656 and the bed position described in the item 658 correspond to each other in a one-to-one manner. However, as shown in FIG. 7 or 8, since each part has a wide range, it is possible to set a plurality of bed positions for one part in order to control the imaging position in each part in more detail. In this case, a scan name is assigned to each bed position. The calculation result of the SAR calculated in step S636 is displayed. As the displayed calculation value of the SAR, there is a case of a predictive calculation result calculated based on (Equation 1) to (Equation 3), and there is also a case of a measurement calculation result calculated based on (Equation 4) to (Equation 6). Although there are three kinds of calculation results of the SAR for each scan name in practice, only one is described by omitting the others. In addition, a value shown as the specified SAR value is a specified value of the SAR that should not be exceeded. Although there are three kinds of specified values of the SAR for each scan name in practice, they are omitted.

An item 662 is a time required for the imaging operation set for each scan name, and is a time for which RF pulses are emitted from the irradiation coil 48. An item 664 is a time for which no imaging is performed including the moving time of the top plate 84 of the bed 82, that is, a time for which no RF pulse is emitted. The sum column of the item 662 or the item 664 is the time of the sum of each item.

An item 666 is the moving speed of the top plate 84 of the bed 82. In addition, the sum column is the sum of the movement time of the top plate 84 of the bed 82. A setting display 872 is a display for determining the input or change result in FIG. 14. When the setting display 872 is selected, the content described in FIG. 14 is set and determined.

As an example for explanation, explanation will be given on the assumption that the description order of the scan name described in the item 654 in FIG. 14 or in the scan list display portion 810 in FIG. 2 is the order of scan A, scan B, and scan C initially and the order of the scan B and the scan C is changed in step S634 in FIG. 13. FIG. 14 shows a state in which the order of the scan B and the scan C has been changed with the cursor 150. When the head is located at the center of the gradient magnetic field first, imaging is started from the head, and is continued in order along the movement of the bed 82 in a direction from the head to the feet. In this manner, the movement time of the bed 82 is short, and the time required for imaging is short. In FIG. 14, if the imaging of the abdomen of the scan C is performed after the imaging of the head of the scan A and then the imaging of the chest of the scan B is performed, the movement direction of the top plate 84 of the bed 82 is changed. As a result, the movement overlaps the former movement. For this reason, if the order of the imaging of the scan B and the scan C is changed, the waiting time according to the movement of the bed 82 is increased. However, by increasing the waiting time, it is possible to reduce the value of the SAR that is the amount of absorption of the energy of RF pulses per unit time.

For the above reasons, if the operator changes the description order of the scan name in the item 654 in FIG. 14, the imaging order is changed based on the operation of the operator, and the movement time of the bed 82 according to the change is automatically calculated. The waiting time obtained by the calculation is displayed in the item 664. The example shown in FIG. 14 is an example of increasing the waiting time for reducing the value of the SAR, which is the amount of absorption of the energy of RF pulses per unit time, by changing the imaging order. In order to reduce the value of the SAR that is the amount of absorption of the energy of RF pulses per unit time, it is important to increase the waiting time, and it is also possible to change the waiting time of the item 664 without changing the imaging order. In this case, for example, the waiting time of the relevant scan name in the item 664 is designated with the cursor 150, and input for increasing the waiting time is performed. If the waiting time is increased, the top plate 84 of the bed 82 is controlled so as to move slowly according to the waiting time, for example. As another example, no RF pulses may be emitted from the irradiation coil 48 until the waiting time elapses even if the movement of the top plate 84 of the bed 82 ends.

The above explanation is relevant to the operation for reducing the value of the SAR that is the amount of absorption of the energy of RF pulses per unit time, and is a method of reducing the value of the SAR that is the amount of absorption of the energy of RF pulses by increasing the waiting time of the scan B or the scan C in the item 664. On the other hand, when the conditions of the SAR are satisfied in step S602, processing for reducing the time required for the imaging of the object 1 by reducing the waiting time on the contrary is performed in step S364. In this case, the value of the waiting time is changed in a decreasing direction. Thus, through the processing in step S634, the waiting time of the item 664 is changed in an increasing direction or in a decreasing direction. In step S635, based on the newly changed imaging schedule, the total time of the item 662 or the item 664 or the moving speed of the bed 82 or the sum of movement time of the item 666 is calculated.

In step S634, the waiting time of the item 664 is increased or decreased as described above. Reducing the time until the imaging is started after the movement of the bed 82 leads to the improvement of the work. In some cases, if the time until the imaging is started after the movement of the bed 82 is stopped is long, object 1 may feel uneasy. Therefore, it is preferable to control the moving speed of the top plate of the bed 82, which is the moving speed of the bed 82, according to the waiting time.

$$\text{Bed moving speed } SB(\text{mm/s}) = \frac{D(\text{mm})}{Tw(s) - \frac{D(\text{mm})}{S0(\text{mm/s})}} + So \quad \text{[Equation 7]}$$

Here, Tw≠D/So. Here, BS (mm/S) is the moving speed of the top plate 84 of the bed 82, Tw (s) is a waiting time, D (mm) is a moving distance, and So (mm/s) is the initial moving speed of the top plate 84. By adjusting the moving speed of the bed based on (Equation 7), it is possible to gently move the object 1 using an increase in the waiting time when the waiting time is increased. Therefore, it is possible to reduce the physical impact of the object 1. In addition, since an increase in the time interval up to the imaging operation after the movement of the bed is stopped can be suppressed, it is possible to reduce the psychological pressure on the object 1. In addition, since the moving speed of the top plate 84 of the bed 82 can be increased within the range satisfying the SAR conditions, the efficiency of the imaging operation is improved. In addition, since it is possible to shorten the total time required for the imaging of the object 1, it is possible to reduce the burden on the object 1 from the overall point of view.

When the waiting time is changed by changing the imaging order or the waiting time of imaging is changed as described above in step S634 shown in FIG. 13, the calculation of the SAR value based on the new conditions is performed in step S636. In step S602, it is determined whether or not the calculated SAR value satisfies the conditions of the SAR. Unlike the embodiment described above, according to the embodiment shown in FIG. 13, it is possible to use the waiting time as a method satisfying the conditions of the SAR. Since the number of solutions for satisfying the conditions of the SAR is increased, a wide range of response including the method described in the above embodiment becomes possible.

Figure 15:
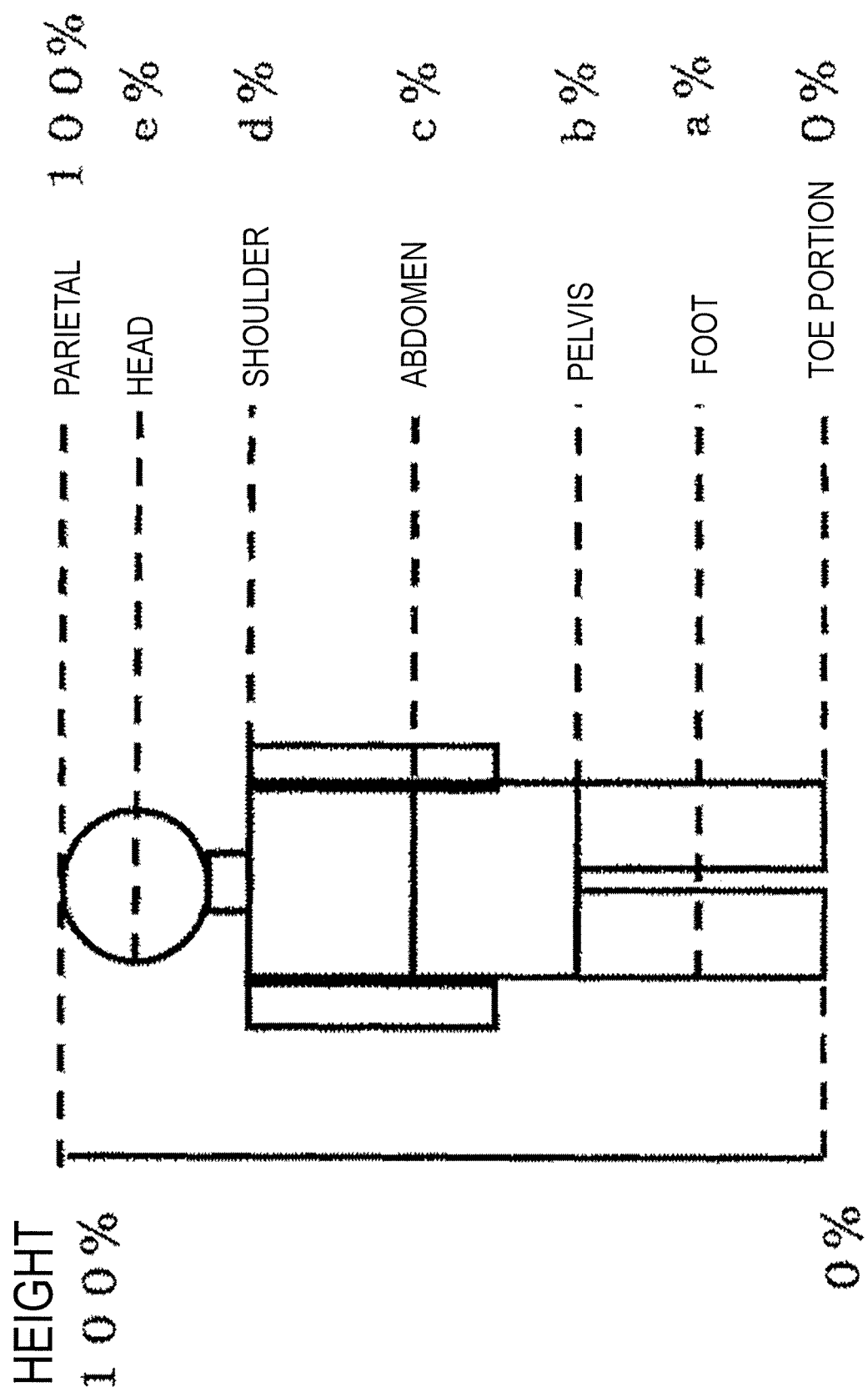
FIG. 15 is a database showing the position information of a standard part.

FIG. 15 shows standard data indicating the relationship between a part and height in the database DB1 shown in FIG. 7 or the database DB2 shown in FIG. 8, and the standard data is stored in the internal memory 66. FIG. 15 shows data in which a toe portion is a reference, the toe portion is disposed at the center of the gradient magnetic field, and the head is located farthest from the center of the gradient magnetic field (hereinafter, referred to as feet first). On the contrary, from this data, data in which the parietal is a reference, the head is disposed at the center of the gradient magnetic field, and the feet are located farthest from the center of the gradient magnetic field (hereinafter, referred to as head first) can be easily obtained by calculation. Using the part data of the standard person shown in FIG. 15, conversion into the information of the unique part position of the object 1 to be imaged can be performed when necessary using the height information of the object 1. For the database DB1 or the database DB2 shown in FIG. 7 or FIG. 8, it is desirable to use the relationship between a part and a bed position or to use the value of the bed position for the standard person in the search process of W-basic, head absorption rate, or W-patient using bed position as a search parameter. Therefore, databases including the database DB1 or the database DB2 are created based on the height or physique of the standard person shown in FIG. 15. On the other hand, when using the data retrieved from these databases, the bed position based on the standard person is used after being converted into the value of the individual object 1.

Figure 16:
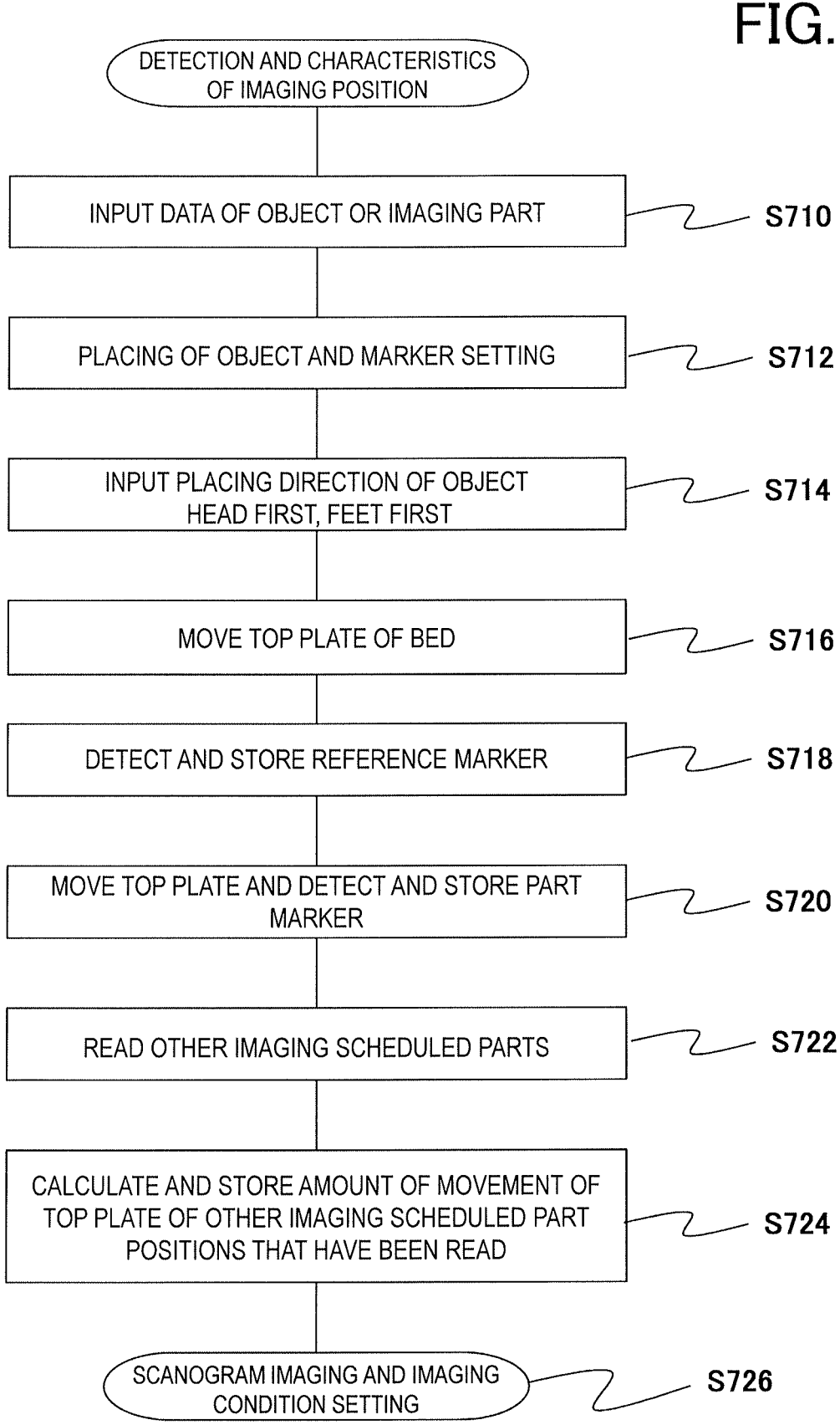
FIG. 16 is a flowchart for converting the position of a part of an object into the moving length of a top plate.

FIG. 16 is a flowchart for converting the position of an input part of the object 1, in which imaging is scheduled, into the moving length of the top plate 84 of the bed 82 or for setting the relationship between a position where the object 1 is placed and the gradient magnetic field center, which is the reference position of the gantry, or the relationship between the position where the object 1 is placed and the reference position of the top plate 84 of the bed 82. In step S710, an imaging scheduled part or personal information of the object 1 is input. As the imaging scheduled part of the object 1, a plurality of parts can be input at a time. For example, as shown in FIG. 2, a scan name is assigned to each of the input parts. Although the imaging scheduled part is input in step S710 in this example, a distance from the reference point in the standard person shown in FIG. 15 or the movement stop position of the top plate 84 may be input for the imaging position instead of a part. In order to input the stop position of the top plate 84 with the individual value of the object 1 that is a person for whom imaging is scheduled, it is necessary to measure the length from the reference point of the imaging position of the object 1 one by one. This is very troublesome. As shown in FIG. 15, it is efficient to input the value based on the standard positional relationship. This is also convenient for data search or the like.

In step S712, the object 1 is placed on the top plate 84 of the bed 82. As a direction in which the object 1 is placed, for example, there is a head first direction in which the head moves to the center of the gantry first as described in FIG. 17 or a feet first direction in which the feet move to the center of the gantry first as described in FIG. 18. In step S712, a marker is attached to the reference position and the part of the object 1. In this case, it is not necessary to attach a marker to all parts to be imaged, and a marker may be attached to one or two places. Then, in step S714, it is input whether the object 1 has been placed in the head first direction with respect to the top plate 84 or placed in the feet first direction. This information is used to calculate the relationship between the input part and the bed position.

Figure 17:
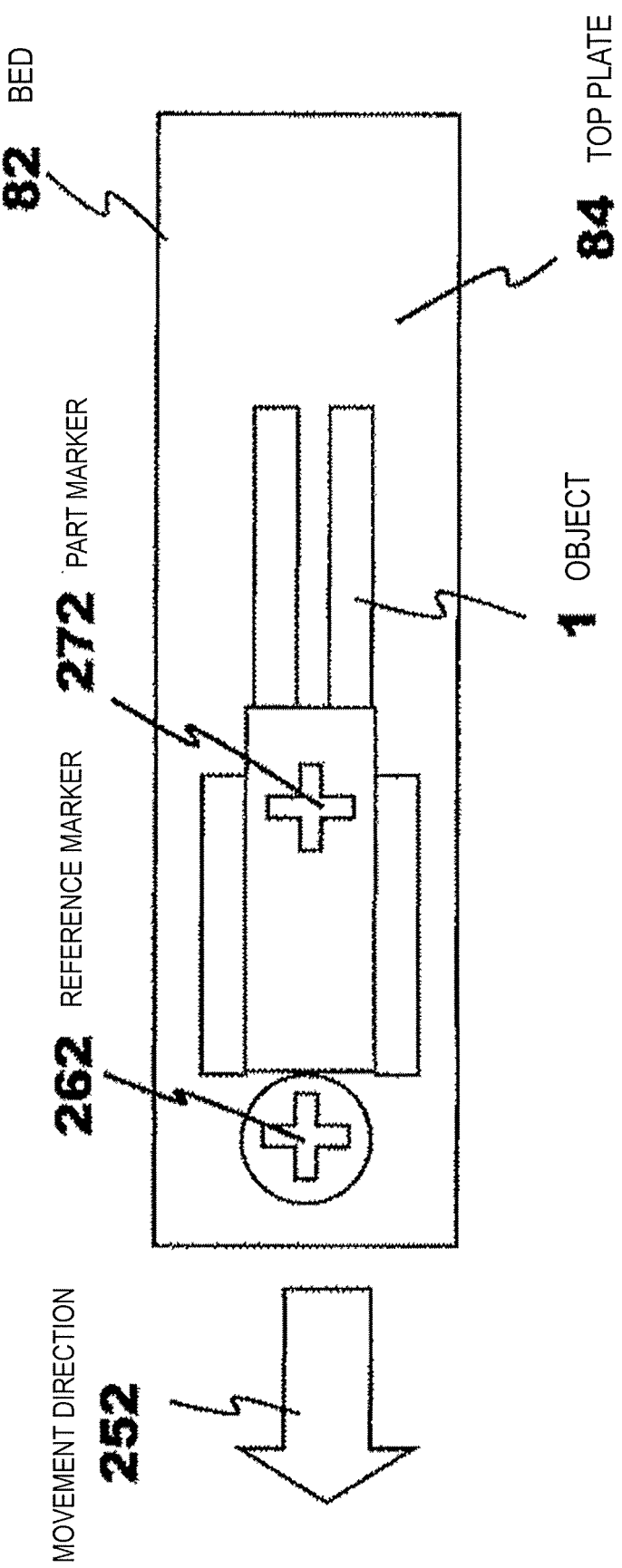
FIG. 17 is an explanatory diagram showing a state in which an object is placed on the top plate of the bed in the head first direction.

In the mounting example described in FIG. 17, a reference marker 262 used as a reference is fixed to the head of the object 1, and a part marker 272 is fixed to the abdomen that is an imaging scheduled part. Not only the part at the position of the part marker 272 but also the part at the fixing position of the reference marker 262 can be imaged. The specification of the positions of other parts to which no marker is attached is also possible from the positional relationship of the reference marker 262 or the part marker 272, and it is possible to perform imaging by stopping the movement of the top plate 84 at the position of the input part.

One method of determining the position of an imaging scheduled part of the object 1 by calculation is a method of measuring the length of the reference marker 262 and the part marker 272 unique to the object 1 from the positional relationship of the reference marker 262 and the part marker 272 and calculating a distance from the reference position of the imaging scheduled part unique to the object 1 by performing a proportional operation based on the difference in the length with respect to the standard database described in FIG. 15. Another method is a method of calculating the distance between the imaging schedule part of the object 1 and the reference marker 262 by calculating the ratio between the input height of the object 1 and the height of the standard data in FIG. 15 and converting the standard distance from the reference position for each input part into the distance unique to the object 1. In the mounting method in FIG. 17, it is possible to stop the top plate at the calculated distance of the imaging scheduled part with the reference marker 262 as a reference point.

Figure 18:
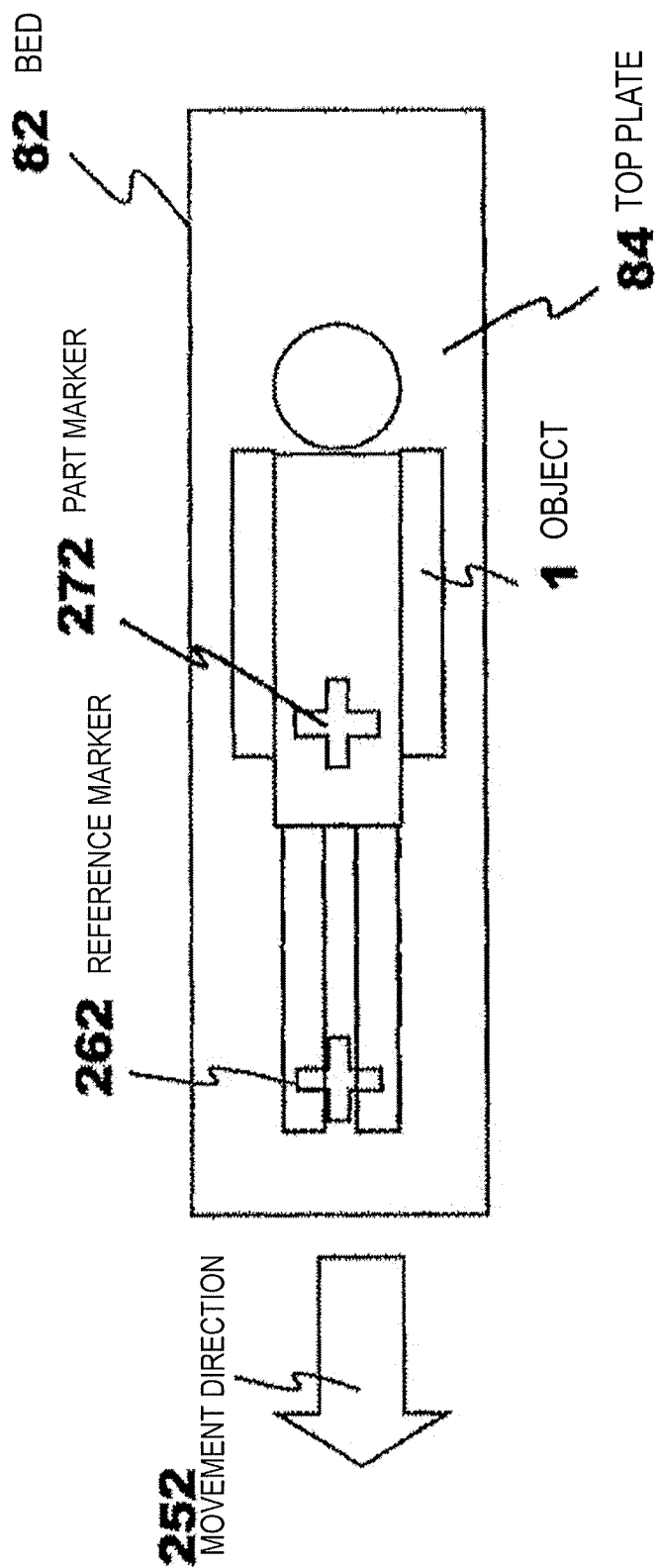
FIG. 18 is an explanatory diagram showing a state in which an object is placed on the top plate of the bed in the feet first direction.

In the example shown in FIG. 18, the reference marker 262 used as a reference is fixed to the feet of the object 1, and the part marker 272 is fixed to the abdomen that is an imaging scheduled part. Also in this example, as described above, by detecting the distance between the reference marker 262 and the part marker 272, it is possible to calculate the personal value of the input position of the imaging scheduled part based on the data in FIG. 15. Therefore, it is possible to control the movement or stop of the top plate 84 based on the personal value of the object 1. In addition, as described above, by using the reference marker 262 and the data of the height of the object 1, it is possible to perform the same operation and control even if the part marker 272 is not used.

In FIG. 17 or 18, a movement direction 252 indicates a movement direction of the top plate 84. When the top plate 84 moves in step S716, the reference marker 262 is first moved to the center position of the gradient magnetic field that is a gantry center. In step S718, the reference marker 262 is detected, and the relationship between the reference position of the top plate 84 and the reference marker 262 is stored. In step S720, the top plate 84 is moved, and the part marker 272 is detected. The positional relationship between the part marker 272 and the reference position of the top plate 84 or the distance information between the reference marker 262 and the part marker 272 is measured and stored.

Then, in step S722, other imaging scheduled parts that have been input are read. In step S724, the distance between each of the read parts and the reference marker 262 or the distance of the top plate 84 from the reference position is calculated by operation, and the calculated value is stored. After step S724, processing required for imaging, such as step S726 in the embodiment that has been previously described, is performed.

Figure 19:
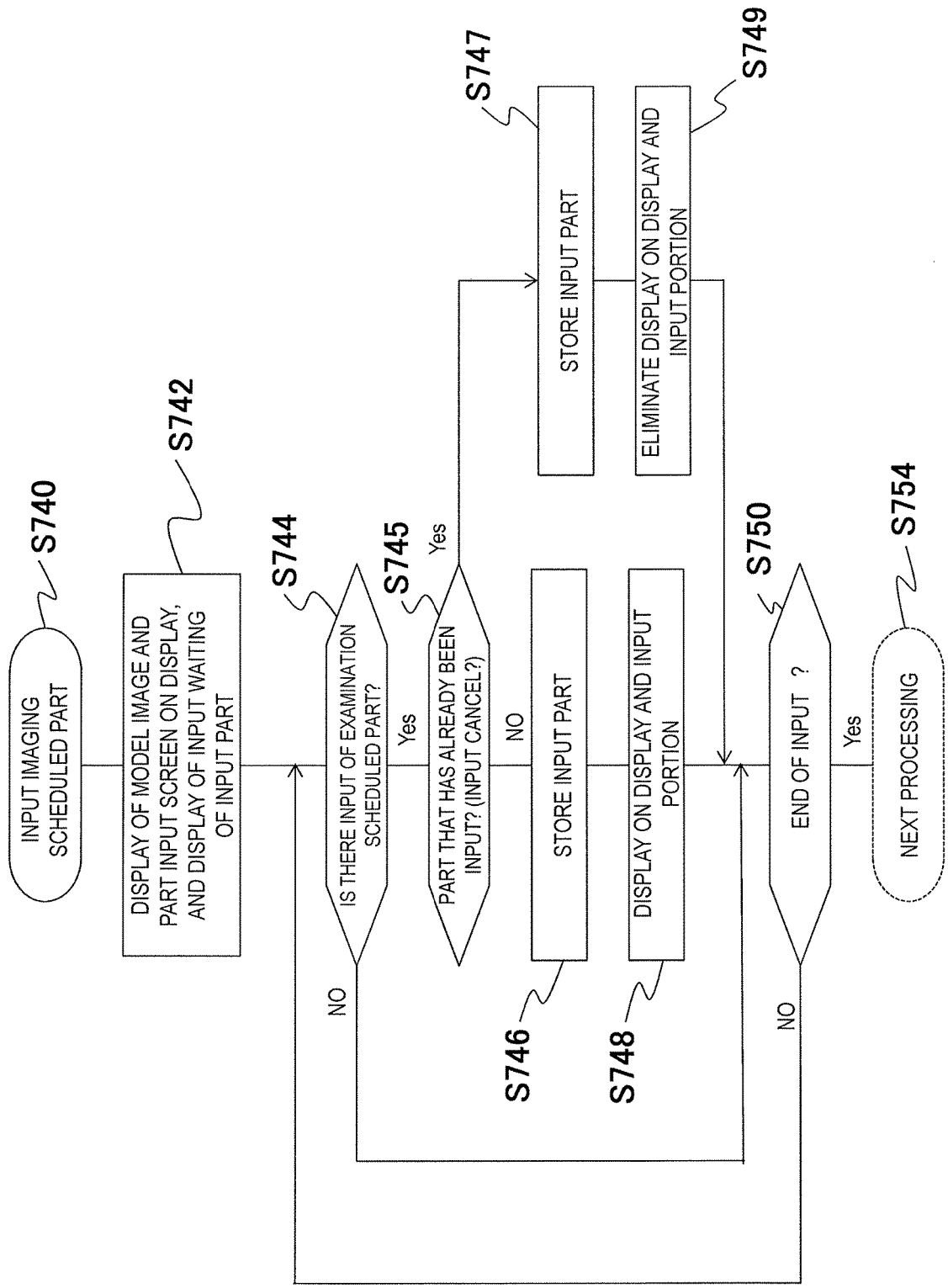
FIG. 19 is a flowchart for inputting a part to be imaged.
Figure 20:
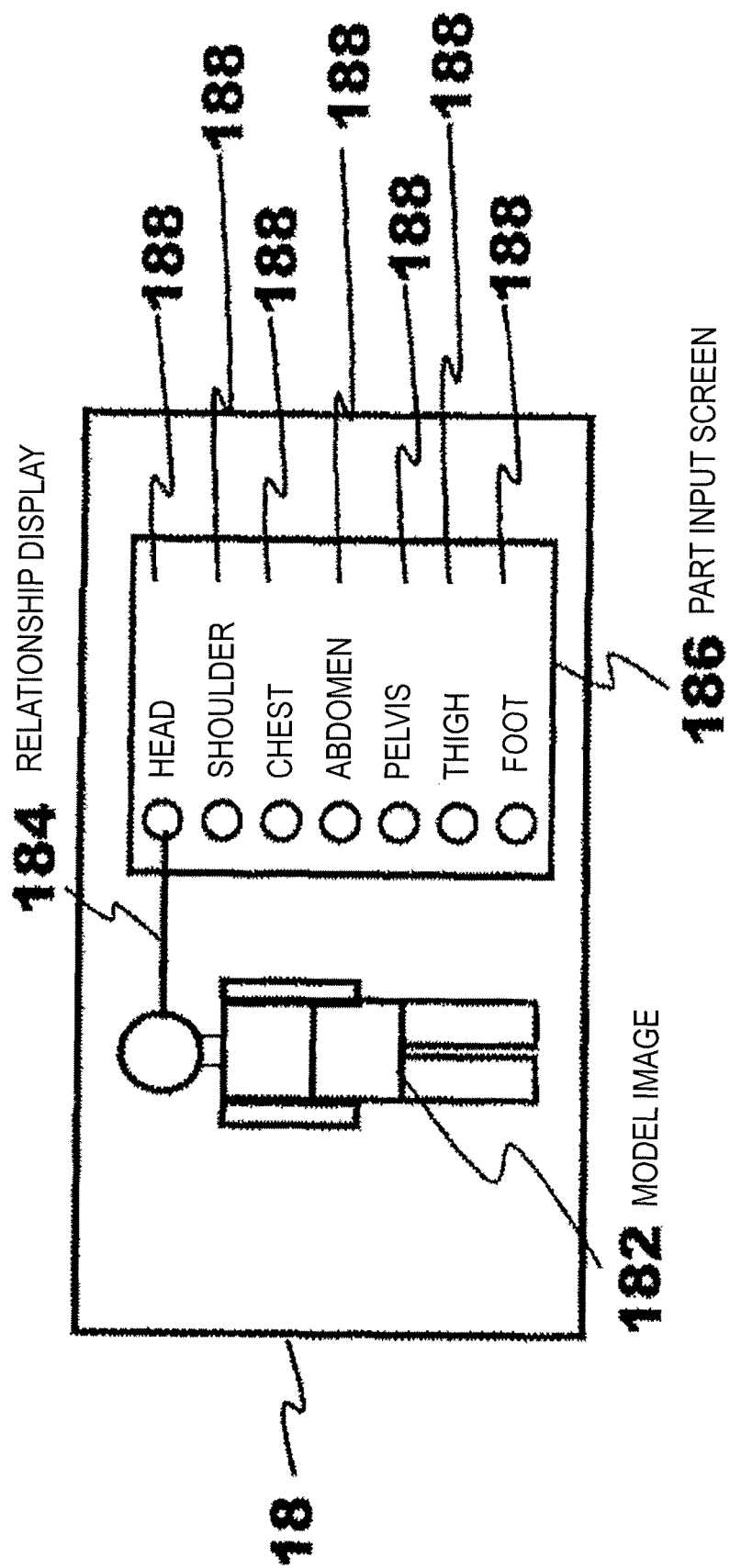
FIG. 20 is a display image on a display provided in a gantry.

FIG. 19 is a flowchart for inputting an imaging scheduled part, and FIG. 20 is an image displayed on the display 18 provided in gantry. The image shown in FIG. 20 is not limited to being displayed on the display 18 provided in the gantry, and may be displayed on a display 98 or may be displayed on both the displays 18 provided in the gantry and the display 98.

In addition, the display 18 provided in the gantry shown in FIG. 20 includes a touch panel or the like. Therefore, not only the display but also the input or cancellation of an imaging scheduled part based on the touching of a displayed image can be performed.

The image displayed on the display 18 provided in the gantry includes a model image 182, a part input image 186, a relationship display 184 showing the relationship between the model image 182 and the part input image 186. In the part input image 186, a part name 188 as an imaging target is displayed. For example, when the head of the part name 188 is selected by an operation, such as a touch, the head that is the selected part name and the head of the model image 182 are connected to each other through the relationship display 184. Therefore, it can be seen that the head has been input as an imaging scheduled part. In the above explanation, an imaging scheduled part is input by designating the part input image 186. However, when an imaging scheduled part is designated for the image of the model image 182, for example, when the head of the model image 182 is touched, the head is input as an imaging scheduled part, and the relationship display 184 is displayed. When the part that has been input is selected again by a touch operation or the like in the model image 182 or the part input image 186, the previous input state is reset, and the relationship display 184 of the target that has been displayed is eliminated. When the imaging scheduled parts are input in order, scan names are assigned in the input order, and are displayed in the scan list display portion 810 in FIG. 2.

Figure 21:
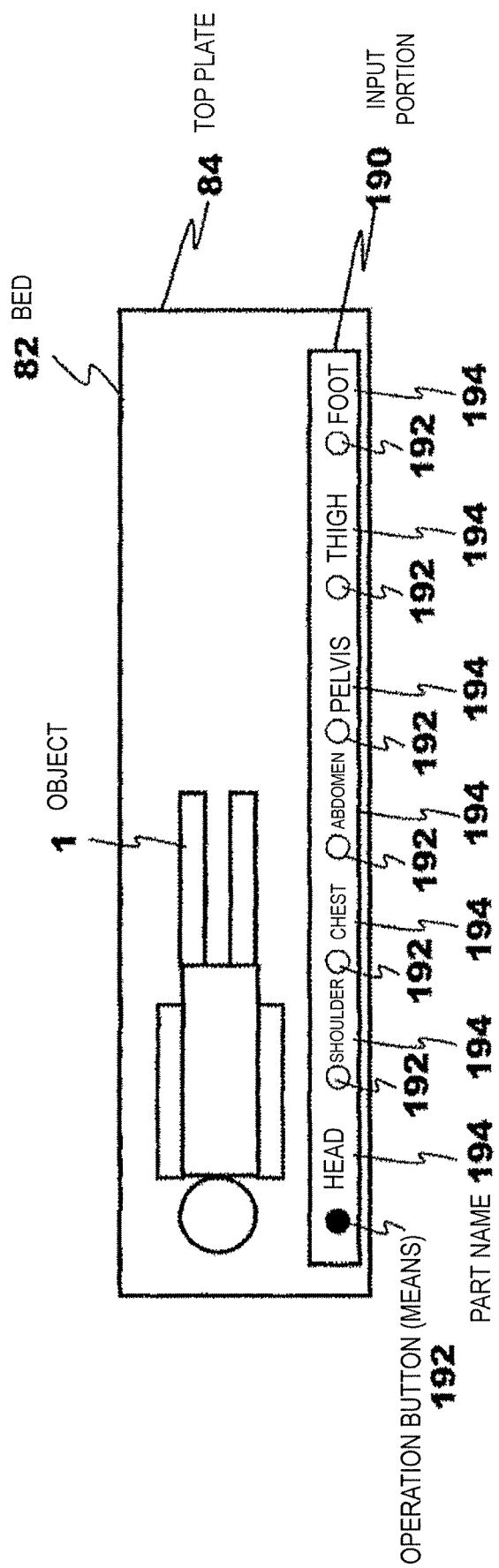
FIG. 21 is an explanatory diagram of an input portion provided in the bed.

FIG. 21 is a diagram for explaining an input portion 190 provided in the top plate 84. Through the input portion 190, it is possible to input or cancel an imaging scheduled part. The input portion 190 has an input function. In addition, an operation button 192 that is an example of an operation means is provided in the input portion 190 corresponding to each part name 194. The color of the operation button 192 that is an example of the operation means is changed in the input state. Accordingly, the input portion 190 also has a function of displaying an input state or a non-input state. When the part names 194 displayed in the input portion 190 are selected in order according to the imaging schedule, the part names are input in order. For example, in order to image the head of the object 1 placed on the top plate 84, when the operation button 192 that is an operation means corresponding to the part name 194 is selected, the color of the operation button 192 is changed and it is displayed that the part of the head has been selected. When a plurality of part names 194 are selected, the colors of the plurality of operation buttons 192 corresponding to the selected part names 194 are changed. Therefore, it can be seen that a plurality of part names have been input.

When both of the input portion 190 shown in FIG. 21 and the part input image 186 or the model image 182 described in FIG. 20 are used, the display state of the operation button 192 of the relevant part name 194 in the input portion 190 is changed to the display of the input state based on the input from the display 18 provided in the gantry. On the contrary, for the input from the input portion 190, the display state becomes a display state showing that the input has been performed in the display 18 provided in the gantry. That is, the relationship display 184 is displayed so that the relationship between the input part name 188 and the model image 182 can be seen. It is possible to perform a resetting operation for returning the part name 188 or the part name 194, which has already been input, to the state in which there is no input from the display 18 provided in the gantry or the input portion 190. Even before the object 1 described in FIG. 21 is placed on the top plate 84 or even after the object 1 described in FIG. 21 is placed on the top plate 84, the input from the input portion 190 is possible.

In addition to the input or display of the imaging scheduled part from the display 18 provided in the gantry that is shown in FIG. 20, the input or display of the imaging scheduled part is also possible in the input portion 190 shown in FIG. 21. The display 18 provided in the gantry that is shown in FIG. 20 or the input portion 190 shown in FIG. 21 is an example of the input or display of the imaging scheduled part, and both of the display 18 and the input portion 190 may be provided or one of them may be provided. Although it is very convenient if they are provided, the function of the input or display of the imaging scheduled part is not essential since the input and output device 90 also has the function.

FIG. 19 is a flowchart for inputting a part to be imaged. When the execution of the flowchart is started in step S740, the model image 182 or the part input image 186 is displayed on the display 18 provided in the gantry in step S742, so that a part can be input on the display 18 provided in the gantry. In addition, an input from the input portion 190 is also possible. The top plate 84 is located in a place where it is easily touched by a person. For this reason, if an input through the input portion 190 is made possible at all times, there is a concern that erroneous input will occur in a state in which the object 1 is placed. Therefore, the erroneous input can be prevented by permitting an input operation as in step S742 or the like.

In step S744, it is checked whether or not there has been an input. When there is an input of a part, step S745 is executed. In step S745, it is detected whether the input part is a new input or a part that has already been input and accordingly an operation of canceling the input. In the present embodiment, input cancel is determined when the input operation is performed again for the state in which there has already been an input. For the first input part, in step S746, the input part is stored. In step S748, the relationship display 184 is displayed on the display 18 provided in the gantry that is described in FIG. 20, and the color of the corresponding operation button 192 of the input portion 190 shown in FIG. 21 is changed. A scan name is assigned to the input part, and the scan name is displayed in the scan list display portion 810 shown in FIG. 2.

On the other hand, when it is determined that re-input has been performed for a part that was already input in step S745, step S747 is executed to eliminate the information of the input part from the storage device. Then, in step S749, the display 184 shown in FIG. 20, which has been displayed on the display 18 provided in the gantry and a means that an input has been completed, is eliminated. In addition, in the input portion 190 shown in FIG. 21, a display showing that this is the input state of the relevant part is changed to a display showing that this is a no-input state. In addition, the relevant scan name displayed in the scan list display portion 810 in FIG. 2 is eliminated.

When no input operation has been performed in step S744, the execution proceeds from step S744 to step S750 to determine whether or not this is a state meaning the end of the part input operation. For example, when an operation meaning the end of the input operation has been performed, it is determined that the input of a part has ended, and the next processing for imaging is performed in step S754. In the case of a state in which a part input operation has not ended, the execution returns to step S744 to determine whether or not the input of a part has been performed.

By inputting a part using the method described in FIG. 19, 20, or 21, it is possible to input a part in a very simple way. For the input part, a scan name is assigned for each input as a part to be imaged. In addition, the input part is displayed in the scan list display portion 810 in FIG. 2, and the imaging conditions are set for each scan name as described above. By searching for the database DB1 of the W-basic or the database DB2 of the W-patient based on the part input as described above, it is possible to calculate the SAR using the data of the W-basic or the data of the W-patient that corresponds to the part. Therefore, it is possible to calculate the predicted SAR value or the measured SAR value with high accuracy. This leads to the setting of the corrected imaging conditions.

REFERENCE SIGNS LIST

1: object
12: sequencer
14: central processing unit (CPU)
15: marker
18: display provided in the gantry
20: static magnetic field generating source
30: magnetic field generating system
32: gradient magnetic field generating coil
34: gradient magnetic field power source
40: transmission system
42: high frequency oscillator
44: modulator
46: high frequency amplifier
48: irradiation coil
50: receiving system
52: receiving coil
54: signal amplifier
56: quadrature phase detector
58: A/D converter
60: signal processing system
61: external storage device
62: optical disc
64: magnetic disc
66: memory
70: SAR calculation unit
80: bed control device
82: bed
84: top plate
90: input and output device
92: pointing device 94: keyboard
96: output device
98: display
99: printer
100: MRI apparatus
150: cursor
152: scan name
182: model image
190: bed input portion
192: operation button
262: reference marker
272: part marker
604: object information storage section
605: object information storage section
606: imaging condition storage section
607: imaging condition storage section
800: setting image
810: scan list display portion
820: selected imaging condition display portion
830: positioning image display portion
832: positioning image
834: scan position
836: scan position
838: imaging section
840: SAR value display portion
842: SAR value
844: specified SAR value
850: imaging parameter display portion
852: repetition time
854: echo time
856: bed position
860: imaging start mark
870: imaging schedule display portion
872: setting display
880: scan order candidate display portion

The invention claimed is:

1. A magnetic resonance imaging apparatus, comprising:
a bed including a top plate that moves an object placed thereon;
a magnetic generation means which generates a magnetic field in a space in which the object is located;
an irradiation coil for irradiating the object with RF pulses;
a receiver which detects an NMR generated by the object and images the detected NMR signal;
an input and output device for inputting or displaying imaging conditions; and
a control device that calculates an amount of absorption of electromagnetic waves caused by the irradiation of the RF pulses to the object based on the input imaging conditions, determines whether or not the calculated amount of absorption satisfies conditions of a specified value of the amount of absorption of electromagnetic waves, and performs movement control of the top plate and irradiation control of the RF pulses in accordance with imaging conditions determined to satisfy the conditions of the specified value of the amount of absorption of electromagnetic waves,
wherein the control device further includes a database of an absorption rate of electromagnetic waves that uses a part of the object to be imagined or a bed position where imaging is scheduled as a search parameter,
wherein the control device reads an absorption rate of electromagnetic waves from the database with the part of the object to be imaged or the bed position where imaging is scheduled as a search parameter, and calculates the amount of absorption of electromagnetic waves in imaging in the part or the bed position using the read absorption rate,
wherein a database of the absorption rate of electromagnetic waves is data indicating an absorption rate of electromagnetic waves of a standard person with a part or a bed position as a search parameter,
wherein data indicating the absorption rate of electromagnetic waves of the standard person is read from the database, with the part of the object to be imaged or the bed position where imaging is scheduled as a search parameter, and
wherein the amount of absorption of the object is calculated using the read data of the absorption rate of electromagnetic waves of the standard person.

2. The magnetic resonance imaging apparatus according to claim 1,
wherein the control device stores position information for imaging in the part of the object or the bed position as information corresponding to the standard person, converts the position information corresponding to the standard person into information corresponding to the object, and controls movement or stop of the top plate of the bed using the converted information corresponding to the object.

3. A control method of a magnetic resonance imaging apparatus including a bed having a top plate that moves an object placed thereon, a magnetic field generation means which generates a magnetic field in a space in which the object is located, an irradiation coil for irradiating the object with RF pulses, a means which detects an NMR signal generated by the object and images the detected NMR signal, an input and output device for inputting or displaying imaging conditions, and a control device, the method comprising:
a first step of calculating an amount of absorption of electromagnetic waves into the object according to the imaging conditions;
a second step of determining whether or not the amount of absorption of electromagnetic waves calculated in the first step satisfies conditions of a specified value of the amount of absorption of electromagnetic waves;
a third step of performing display indicating that the conditions are not satisfied when the calculated amount of absorption of electromagnetic waves does not satisfy the conditions of the specified value of the amount of absorption of electromagnetic waves;
a fourth step of calculating the amount of absorption of electromagnetic waves into the object according to newly input imaging conditions and determining whether or not the amount of absorption of electromagnetic waves based on the newly input imaging conditions satisfies the conditions of the specified value of the amount of absorption of electromagnetic waves; and
a fifth step of performing movement control of the top plate and irradiation control of the RF pulses under the imaging conditions satisfying the conditions when the amount of absorption of electromagnetic waves based on the newly input imaging conditions satisfies the conditions of the specified value of the amount of absorption of electromagnetic waves.

* * * * *